(12) United States Patent
Mealey

(10) Patent No.: US 7,393,643 B2
(45) Date of Patent: Jul. 1, 2008

(54) METHOD OF DETECTING IVERMECTIN SENSITIVITY IN A CANINE SUBJECT BY IDENTIFYING A MUTATION IN A MDR1-ENCODING SEQUENCE

(75) Inventor: Katrina L. Mealey, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 339 days.

(21) Appl. No.: 10/896,434

(22) Filed: Jul. 21, 2004

(65) Prior Publication Data

US 2004/0265896 A1  Dec. 30, 2004

Related U.S. Application Data

(62) Division of application No. 10/044,671, filed on Jan. 10, 2002, now Pat. No. 6,790,621.

(60) Provisional application No. 60/314,829, filed on Aug. 24, 2001, provisional application No. 60/261,578, filed on Jan. 12, 2001.

(51) Int. Cl.
 *C12Q 1/68* (2006.01)
 *C07H 21/04* (2006.01)

(52) U.S. Cl. .............................. 435/6; 435/6; 435/91.2; 536/23.1; 536/23.5; 536/24.31; 536/24.33

(58) Field of Classification Search ....................... None
See application file for complete search history.

(56) References Cited

U.S. PATENT DOCUMENTS 5,583,008 A  12/1996 Johnson et al.
6,790,621 B2 *  9/2004 Mealey et al. ................... 435/6

FOREIGN PATENT DOCUMENTS

| WO | WO 94/26115 | 11/1994 |
| WO | WO 98/13072 | 4/1998 |
| WO | WO 98/14615 | 4/1998 |
| WO | WO 00/46347 | 8/2000 |
| WO | WO 00/52144 | 9/2000 |
| WO | WO 01/09183 | 2/2001 |

OTHER PUBLICATIONS

Brown et al. of J. Tropical Medicine and Parasitology, 1998, 92: S61-S64.*
Mealey et al. Pharmacogenetics 2001, 11:727-733.*
van Helvoort et al., Cell, 1996, 87: 507-517.*
Schinkel et al., Cell 77: 491-502.*
Sparreboom et al., 1997, PNAS 94: 2031-2035.*
Paul et al. (Veterinary Parasitology, vol. 121, pp. 285-291, 2004).*
Takara et al. (Biol. Pharm. Bull. vol. 25, No. 6, pp. 771-778, 2002).*
Griffin et al. (J. Vet. Pharmacol. Therap. vol. 28, pp. 257-265, 2005).*
Geyer et al. (J. Vet Pharmacol. Therp. vol. 28, pp. 95-99, 2005).*
Taub et al. (Drug Metabolism and Disposition, vol. 33, pp. 1679-1687, 2005).*
Mealey et al. (JAVMA, vol. 223, No. 10, p. 1453,Nov. 2003).*

Henik et al. (J. Vet. Intern Med, vol. 20, pp. 415-417, 2006).*
Brown et al, "Changes in the use profile of Mectizan: 1987-1997," *Journals of Tropical Medicine & Parasitology* 92(1):S61-S64, 1998.
Campbell et al, "Molecular cloning and characterization of canine metalloproteinase-9 gene promoter," *Gene* 273(1):81-87, 2001 Abstract Only.
Carver et al, "Mutagenicity Testing in Mammalian Cells," *Mutation Research* 72:207-230, 1980.
Decleves et al, "A new polymorphism (N21D) in the exon 2 of the human MDR1 gene encoding the P-glycoprotein," *Human Mutation* 15(5):486, 2000.
Fassler et al, "Evaluation of the safety of ivermectin administered in a beef-based formulation to ivermectin-sensitive Collies," *J Am Vet Med Assoc* 199(4):457-460, 1991, Abstract Only.
Hoerauf et al, "Tetracycline therapy targets intracellular bacteria in the filarial nematode Litomosoides sigmodontis and results in filarial infertility," *J Clin Invest* 103(1):11-17, 1999.
Hoffmeyer et al, "Functional polymorphisms of the human multidrug-resistance gene: Multiple sequence variations and correlation of one allele with P-glycoprotein expression and activity in vivo." *PNAS* 97(7):3473-3478, 2000.
Jun et al., "Insertion of a retroviral solo long terminal repeat in mdr-3 locus disrupts mRNA splicing in mice,"*Mammal. Gen.* 11(10):843-848, Oct. 2000.
Kadoi, "Establishment of a canine monocyte cell line," *New Microbiol* 23(4):441-444, 2000 Abstract Only.
Kim et al, "The Drug Transporter P-glycoprotein Limits Oral Absorption and Brain Entry of HIV-1 Protease Inhibitors," *J Clin Invest* 101(2):289-294, 1998.
Knutsen et al, "Cytogenetic and molecular characterization of random chromosomal rearrangements activating the drug resistance gene, *MDR1/P-glycoprotein*, in drug-selected cell lines and patients with drug refractory All," *Genes, Chromosomes and Cancer* 23(1):44-54, 1998 Abstract Only.
Lankas et al, "P-Glycoprotein Deficiency in a Subpopulation of CF-1 Mice Enhances Avermectin-Induced Neurotoxicity," *Toxicology and Applied Pharmacology* 143:357-365, 1997.
Martinez et al, "Neuromuscular Effects of Doxacurium Chloride in Isoflurane-Anesthetized Dogs," *Veterinary Surgery* 27:279-283, 1998 Abstract Only.
Mayer et al, "Full Blockade of Intestinal P-glycoprotein and Extensive Inhibition of Blood-brain Barrier P-glycoprotein by Oral Treatment of Mice with PSC833," *J Clin Invest* 100(10):2430-2436, 1997.
Mealey et al., "Frequency of the mutant MDR1 allele associated with ivermectin sensitivity in a sample population of Collies from the northwestern United States," *Am. J. Vet. Res.* 63(4):479-481, Apr. 2002.
Mealey et al., "Ivermectin sensitivity in collies is associated with a deletion mutation of the mrd1 gene," *Pharmacogen.* 11(8):727-733, Nov. 2001.
Rohrer and Evans, "Binding characteristics of ivermectin in plasma from collie dogs," *Vet Res Commun* 14(2):157-165, 1990 Abstract Only.

(Continued)

*Primary Examiner*—Jeanine A. Goldberg
(74) *Attorney, Agent, or Firm*—Klarquist Sparkman, LLP.

(57) ABSTRACT

This invention provides the identification of a truncation polymorphism of the mdr1 gene that is linked to ivermectin sensitivity in subjects, such as collies. Also provided are methods for detecting drug transport sensitivity in a subject, and animal models and in vitro cell systems using cells from animals having an mdr1 truncation.

13 Claims, 2 Drawing Sheets

OTHER PUBLICATIONS

Roulet et al., "MDR pharmacogenetics in dog. Molecular basis of antiparasitic drug sensitivity (Ivermectin) in collie dog." *ABC 2001—3rd FEBS Advanced Lecture Course* Mar. 2001 (4 pages).

Ruetz et al., "Functional expression of P-glycoprotein encoded by the mouse mdr3 gene in yeast cells," *Proc. Natl. Acad. Sci. USA* 90(24):11588-11592, 1993.

Pippert et al., "The subpopulation of CF-1 mice deficient in P-glycoprotein contains a murine retroviral insertion in the mdr1a gene," *J. Biochem. Mol. Toxicol.* 15(2):83-89, 2001.

Schinkel et al, "Absence of the mdr1a P-Glycoprotein in mice affects tissue distribution and pharmacokinetics of dexamethasone, digoxin, and cyclosporine A," *J Clin Invest* 96(4):1698-1705, 1995 Abstract Only.

Schinkel et al., "Disruption of the mouse mdr1a P-glycoprotein gene leads to a deficiency in the blood-brain barrier and to increased sensitivity to drugs," *Cell* 77(4):491-502, 1994.

Schinkel et al., "N-glycosylation and deletion mutants of the human MDR1 P-glycoprotein," *J. Biol. Chem.* 268(10):7474-7481, 1993.

Schinkel et al., "P-Glycoprotein in the Blood-Brain Barrier of Mice Influences the Brain Penetration and Pharmacological Activity of Many Drugs," *J Clin Invest* 97(11):2517-2524, 1996.

Smit et al, "Absence or pharmacological blocking of placental P-glycoprotein profoundly increases fetal drug exposure," *J Clin Invest* 104(10):1441-1447, 1999.

Smith et al, "P-Glycoprotein Efflux at the Blood-Brain Barrier Mediates Differences in Brain Disposition and Pharmacodynamics between Two Structurally Related Neurokinin-1 Receptor Antagonists," *JPET* 298(3):1252-1259, 2001.

Suzuki and Sugiyama, "Role of metabolic enzymes and efflux transporters in the absorption of drugs from the small intestine," *Euro. J. Pharma. Sci.* 12:3-12, 2000.

Tranquilli et al, "Ivermectin plasma concentrations in collies sensitive to ivermectin-induced toxicosis," *Am J Vet Res* 50(5):769-770, 1989 Abstract Only.

Umbenhauer et al, "Identification of a P-Glycoprotein-Deficient Subpopulation in the CF-1 Mouse Strain Using a Restriction Fragment Length Polymorphism," *Toxic. Appl. Pharma.* 146:88-94, 1997.

Vaughn et al, "Determination of homovanillic acid, 5-hydroxyindoleacetic acid and pressure in the cerebrospinal fluid of collie dogs following administration of ivermectin," *Vet Res Commun* 13(1):47-55, 1989 Abstract Only.

http://www.dog-tracker.com/forums/vet/messages/10052.shtml, 7 pages, printed Nov. 18, 2000.

http://www.faqs.org/faqs/dogs-faq/breeds/collies, 2 pages, printed Nov. 18, 2000.

http://www.golden-retriever.com/heartwrm.html, 4 pages, printed Nov. 18, 2000.

* cited by examiner

FIGURE 2

```
275 TGGTTTTTGGAAACATGACAGATAGCTTTGCAAATGCAGGAATTTCAAGAAACAAAACTTTT 336
    TGGTTTTTGGAAACATGAC----AGCTTTGCAAATGCAGGAATTTCAAGAAACAAAACTTTT

337 CCAGTTATAATTAATGAAAGTATTACGAACAATACACAACATTTCATCAACCATCTGGAGGA 398
    CCAGTTATAATTAATGAAAGTATTACGAACAATACACAACATTTCATCAACCATCTGGAGGA

399 GGAAATGACCACGTATGCCTATTATTACAGTGGGATCGGTGCTGGCGTGCTGGTGGCTGCTT 460
    GGAAATGACCACGTATGCCTATTATTACAGTGGGATCGGTGCTGGCGTGCTGGTGGCTGCTT

461 ACATCCAGGTTTCATTCTGGTGCCTGGCAGCAGGAAGACAGATACTCAAAATTAGAAAACAA 522
    ACATCCAGGTTTCATTCTGGTGCCTGGCAGCAGGAAGACAGATACTCAAAATTAGAAAACAA

523 TTTTTTCATGCTATCATGCGACAGGAGATTGGCTGGTTTGACGTGCATGACGTTGGGGAGCT 584
    TTTTTTCATGCAATCATGCGACAGGAGATTGGCTGGTTTGACGTGCATGACGTTGGGGAGCT

585 TAACACCCGGCTCACAGACGATGTCTCCAAAATCAATGAAGGAATTGGCGACAAAGTTGGAA 646
    TAACACCCGGCTCACAGACGATGTCTCCAAAATCAATGAAGGAATTGGCGACAAAATTGGAA

647 TGTTCTTTCAATCAATAGCAACATTTTTCACCCGGTTTTATAGTGGGGGTTTACACGTGGTT 708
    TGTTCTTTCAATCAATAGCAACATTTTTCACCCGGTTTTATAGTGGGGGTTTACACGTGGTT
```

FIGURE 3

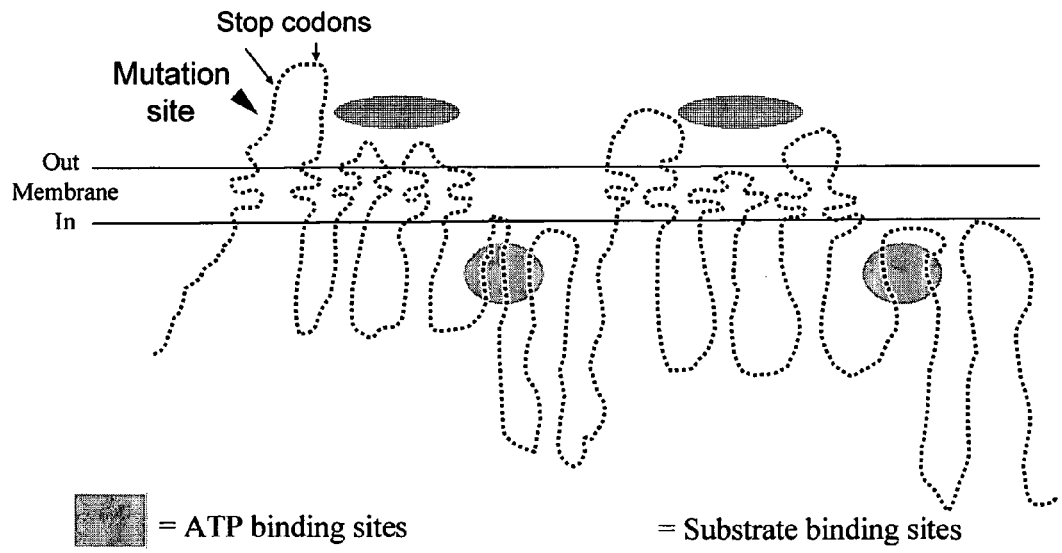

SEQUENCE LISTING

```
<160> NUMBER OF SEQ ID NOS: 10

<210> SEQ ID NO 1
<211> LENGTH: 4317
<212> TYPE: DNA
<213> ORGANISM: Canis familiaris
<220> FEATURE:
<221> NAME/KEY: CDS
<222> LOCATION: (70)..(3912)
<223> OTHER INFORMATION:

<400> SEQUENCE: 1
ctaagtcgga gtatcttctt cccaaattcc cttctcggtg gaggttgcga aggaaagccc         60 gaggtgacg atg gat cct gaa gga ggc cgt aag ggg agt gca gag aag aac        111
           Met Asp Pro Glu Gly Gly Arg Lys Gly Ser Ala Glu Lys Asn
             1               5                  10 ttc tgg aaa atg ggc aaa aaa agt aaa aaa gag aag aaa gaa aag aaa          159
Phe Trp Lys Met Gly Lys Lys Ser Lys Lys Glu Lys Lys Glu Lys Lys
 15                  20                  25                  30 cca act gtc agc acg ttt gca atg ttt cgc tat tca aat tgg ctt gat          207
Pro Thr Val Ser Thr Phe Ala Met Phe Arg Tyr Ser Asn Trp Leu Asp
                 35                  40                  45 agg ttg tat atg ttg gtg ggg aca atg gct gcc atc atc cat gga gct          255
Arg Leu Tyr Met Leu Val Gly Thr Met Ala Ala Ile Ile His Gly Ala
             50                  55                  60 gca ctc cct ctc atg atg ctg gtt ttt gga aac atg aca gat agc ttt          303
Ala Leu Pro Leu Met Met Leu Val Phe Gly Asn Met Thr Asp Ser Phe
         65                  70                  75 gca aat gca gga att tca aga aac aaa act ttt cca gtt ata att aat          351
Ala Asn Ala Gly Ile Ser Arg Asn Lys Thr Phe Pro Val Ile Ile Asn
     80                  85                  90 gaa agt att acg aac aat aca caa cat ttc atc aac cat ctg gag gag          399
Glu Ser Ile Thr Asn Asn Thr Gln His Phe Ile Asn His Leu Glu Glu
 95                 100                 105                 110 gaa atg acc acg tat gcc tat tat tac agt ggg atc ggt gct ggc gtg          447
Glu Met Thr Thr Tyr Ala Tyr Tyr Tyr Ser Gly Ile Gly Ala Gly Val
                115                 120                 125 ctg gtg gct gct tac atc cag gtt tca ttc tgg tgc ctg gca gca gga          495
Leu Val Ala Ala Tyr Ile Gln Val Ser Phe Trp Cys Leu Ala Ala Gly
            130                 135                 140 aga cag ata ctc aaa att aga aaa caa ttt ttt cat gct atc atg cga          543
Arg Gln Ile Leu Lys Ile Arg Lys Gln Phe Phe His Ala Ile Met Arg
        145                 150                 155 cag gag att ggc tgg ttt gac gtg cat gac gtt ggg gag ctt aac acc          591
```

```
Gln Glu Ile Gly Trp Phe Asp Val His Asp Val Gly Glu Leu Asn Thr
    160                 165                 170 cgg ctc aca gac gat gtc tcc aaa atc aat gaa gga att ggc gac aaa         639
Arg Leu Thr Asp Asp Val Ser Lys Ile Asn Glu Gly Ile Gly Asp Lys
175                 180                 185                 190 gtt gga atg ttc ttt caa tca ata gca aca ttt ttc acc ggt ttt ata         687
Val Gly Met Phe Phe Gln Ser Ile Ala Thr Phe Phe Thr Gly Phe Ile
                195                 200                 205 gtg ggg ttt aca cct ggt tgg aag cta acc ctt gtg att ttg gcc atc         735
Val Gly Phe Thr Pro Gly Trp Lys Leu Thr Leu Val Ile Leu Ala Ile
            210                 215                 220 agc cct gtt ctt gga ctt tca gcc gcc atc tgg gca aag ata cta tct         783
Ser Pro Val Leu Gly Leu Ser Ala Ala Ile Trp Ala Lys Ile Leu Ser
        225                 230                 235 tca ttt act gat aaa gaa ctc ttg gcc tat gca aaa gct gga gca gta         831
Ser Phe Thr Asp Lys Glu Leu Leu Ala Tyr Ala Lys Ala Gly Ala Val
    240                 245                 250 gct gaa gaa gtc tta gca gca atc aga act gtg att gcc ttt gga gga         879
Ala Glu Glu Val Leu Ala Ala Ile Arg Thr Val Ile Ala Phe Gly Gly
255                 260                 265                 270 caa aag aaa gaa ctt gaa agg tac aac aaa aat tta gaa gaa gct aaa         927
Gln Lys Lys Glu Leu Glu Arg Tyr Asn Lys Asn Leu Glu Glu Ala Lys
                275                 280                 285 aga att ggg ata aag aaa gct atc acg gcc aac att tct att ggt gcc         975
Arg Ile Gly Ile Lys Lys Ala Ile Thr Ala Asn Ile Ser Ile Gly Ala
            290                 295                 300 gct ttc tta ttg atc tat gca tca tat gct ctg gct ttc tgg tat ggg        1023
Ala Phe Leu Leu Ile Tyr Ala Ser Tyr Ala Leu Ala Phe Trp Tyr Gly
        305                 310                 315 acc tcc ttg gtc ctc tcc agt gaa tat act att gga cag gta ctc act        1071
Thr Ser Leu Val Leu Ser Ser Glu Tyr Thr Ile Gly Gln Val Leu Thr
    320                 325                 330 gtc ttc ttt tct gta tta att ggg gct ttt agt att gga cag gca tcc        1119
Val Phe Phe Ser Val Leu Ile Gly Ala Phe Ser Ile Gly Gln Ala Ser
335                 340                 345                 350 cca agc att gaa gca ttt gca aac gca aga gga gca gct tat gaa atc        1167
Pro Ser Ile Glu Ala Phe Ala Asn Ala Arg Gly Ala Ala Tyr Glu Ile
                355                 360                 365 ttc aag ata att gac aat aaa cca agc att gac agc tat tcg aag agt        1215
Phe Lys Ile Ile Asp Asn Lys Pro Ser Ile Asp Ser Tyr Ser Lys Ser
            370                 375                 380 gga cat aaa cca gat aat att aag gga aat ttg gaa ttc aaa aat gtt        1263
Gly His Lys Pro Asp Asn Ile Lys Gly Asn Leu Glu Phe Lys Asn Val
        385                 390                 395 cac ttc agt tac cct tct cga aaa gaa gtt aag atc tta aag ggt ctc        1311
His Phe Ser Tyr Pro Ser Arg Lys Glu Val Lys Ile Leu Lys Gly Leu
    400                 405                 410 aac ctg aag gtt cag agt ggg cag aca gtg gcg ctg gtt ggg aac agt        1359
Asn Leu Lys Val Gln Ser Gly Gln Thr Val Ala Leu Val Gly Asn Ser
415                 420                 425                 430 ggc tgc ggg aag agc acg acc gtg cag ctg atg cag agg ctc tat gac        1407
Gly Cys Gly Lys Ser Thr Thr Val Gln Leu Met Gln Arg Leu Tyr Asp
                435                 440                 445 ccc aca gat ggc atg gtc tgt att gat gga cag gac att agg acc ata        1455
Pro Thr Asp Gly Met Val Cys Ile Asp Gly Gln Asp Ile Arg Thr Ile
            450                 455                 460 aat gta agg cat ctt cgg gaa att act ggt gtg gtg agt cag gag cct        1503
Asn Val Arg His Leu Arg Glu Ile Thr Gly Val Val Ser Gln Glu Pro
        465                 470                 475
```

```
gtg ttg ttt gcc acc acg ata gct gaa aac att cgc tat ggc cgc gaa   1551
Val Leu Phe Ala Thr Thr Ile Ala Glu Asn Ile Arg Tyr Gly Arg Glu
    480             485                 490 aat gtc acc atg gat gag att gag aaa gct gtt aag gaa gcc aat gcc   1599
Asn Val Thr Met Asp Glu Ile Glu Lys Ala Val Lys Glu Ala Asn Ala
495             500                 505                 510 tat gat ttt atc atg aaa cta cct aat aaa ttt gac act ctg gtt gga   1647
Tyr Asp Phe Ile Met Lys Leu Pro Asn Lys Phe Asp Thr Leu Val Gly
                515                 520                 525 gag aga ggg gcc cgg ctg agt ggt gga cag aaa cag aga atc gcc att   1695
Glu Arg Gly Ala Arg Leu Ser Gly Gly Gln Lys Gln Arg Ile Ala Ile
            530                 535                 540 gct cgg gcc ctg gtt cgc aac ccc aag att ctt ctg ctg gat gag gca   1743
Ala Arg Ala Leu Val Arg Asn Pro Lys Ile Leu Leu Leu Asp Glu Ala
        545                 550                 555 acg tca gct ctg gac act gaa agt gaa gca gtg gtt cag gtg gcc ctg   1791
Thr Ser Ala Leu Asp Thr Glu Ser Glu Ala Val Val Gln Val Ala Leu
    560                 565                 570 gat aag gcc aga aaa ggc cgg act acc att gtg ata gct cat cgt ttg   1839
Asp Lys Ala Arg Lys Gly Arg Thr Thr Ile Val Ile Ala His Arg Leu
575             580                 585                 590 tct aca gtt cgt aat gcc gat gtc att gct ggt ttt gat gat gga gtc   1887
Ser Thr Val Arg Asn Ala Asp Val Ile Ala Gly Phe Asp Asp Gly Val
                595                 600                 605 att gtg gag aaa gga aat cat gat gaa ctc atg aaa gag aag ggc att   1935
Ile Val Glu Lys Gly Asn His Asp Glu Leu Met Lys Glu Lys Gly Ile
            610                 615                 620 tac ttc aaa ctt gtc aca atg cag aca aga gga aat gaa att gag tta   1983
Tyr Phe Lys Leu Val Thr Met Gln Thr Arg Gly Asn Glu Ile Glu Leu
        625                 630                 635 gaa aat gcc act ggt gaa tcc aaa agt gaa agt gat gcc ttg gaa atg   2031
Glu Asn Ala Thr Gly Glu Ser Lys Ser Glu Ser Asp Ala Leu Glu Met
    640                 645                 650 tct cca aaa gat tca ggg tcc agt tta ata aaa aga aga tca act cgc   2079
Ser Pro Lys Asp Ser Gly Ser Ser Leu Ile Lys Arg Arg Ser Thr Arg
655             660                 665                 670 agg agt ata cat gca cca caa ggc caa gac aga aag ctt ggt aca aaa   2127
Arg Ser Ile His Ala Pro Gln Gly Gln Asp Arg Lys Leu Gly Thr Lys
                675                 680                 685 gag gac ttg aat gag aat gtt cct tca gtt tcc ttc tgg agg att ctg   2175
Glu Asp Leu Asn Glu Asn Val Pro Ser Val Ser Phe Trp Arg Ile Leu
            690                 695                 700 aag ctg aac tca act gaa tgg cct tat ttt gtg gtt ggt ata ttt tgt   2223
Lys Leu Asn Ser Thr Glu Trp Pro Tyr Phe Val Val Gly Ile Phe Cys
        705                 710                 715 gct att ata aac gga ggc ctg caa cca gca ttt tca ata ata ttt tca   2271
Ala Ile Ile Asn Gly Gly Leu Gln Pro Ala Phe Ser Ile Ile Phe Ser
    720                 725                 730 agg att ata ggg atc ttt acc cga gat gag gat cct gaa aca aaa cga   2319
Arg Ile Ile Gly Ile Phe Thr Arg Asp Glu Asp Pro Glu Thr Lys Arg
735             740                 745                 750 cag aat agt aac atg ttt tct gta ttg ttt cta gtc ctt gga att att   2367
Gln Asn Ser Asn Met Phe Ser Val Leu Phe Leu Val Leu Gly Ile Ile
                755                 760                 765 tct ttt att aca ttt ttc ctc cag ggc ttc aca ttt ggc aaa gct ggg   2415
Ser Phe Ile Thr Phe Phe Leu Gln Gly Phe Thr Phe Gly Lys Ala Gly
            770                 775                 780 gag atc ctc act aag cgg ctt cga tac atg gtt ttc aga tcc atg ctg   2463
Glu Ile Leu Thr Lys Arg Leu Arg Tyr Met Val Phe Arg Ser Met Leu
        785                 790                 795
```

```
aga cag gat gtc agc tgg ttt gat gac cct aaa aac acc act gga gca     2511
Arg Gln Asp Val Ser Trp Phe Asp Asp Pro Lys Asn Thr Thr Gly Ala
    800                 805                 810 ttg aca acc agg ctt gcc aat gat gcg gct caa gtt aaa ggg gct ata     2559
Leu Thr Thr Arg Leu Ala Asn Asp Ala Ala Gln Val Lys Gly Ala Ile
815                 820                 825                 830 ggt tcc agg ctt gct gtc att acc cag aat ata gca aat ctt ggg aca     2607
Gly Ser Arg Leu Ala Val Ile Thr Gln Asn Ile Ala Asn Leu Gly Thr
                835                 840                 845 ggc att att ata tcc tta atc tat ggt tgg caa tta aca ctt tta ctc     2655
Gly Ile Ile Ile Ser Leu Ile Tyr Gly Trp Gln Leu Thr Leu Leu Leu
        850                 855                 860 tta gca att gta ccc atc att gca ata gca gga gtt gtt gaa atg aaa     2703
Leu Ala Ile Val Pro Ile Ile Ala Ile Ala Gly Val Val Glu Met Lys
                865                 870                 875 atg ttg tct gga caa gca ctg aaa gat aag aaa gag cta gaa gga gct     2751
Met Leu Ser Gly Gln Ala Leu Lys Asp Lys Lys Glu Leu Glu Gly Ala
        880                 885                 890 ggg aag att gct aca gaa gcc atc gaa aac ttc cga act gtt gtt tct     2799
Gly Lys Ile Ala Thr Glu Ala Ile Glu Asn Phe Arg Thr Val Val Ser
895                 900                 905                 910 ttg act cgg gag cag aag ttt gaa tac atg tat gca cag agt ttg caa     2847
Leu Thr Arg Glu Gln Lys Phe Glu Tyr Met Tyr Ala Gln Ser Leu Gln
                915                 920                 925 gta cca tac aga aac tct ttg agg aaa gca cac atc ttc ggg gtc tca     2895
Val Pro Tyr Arg Asn Ser Leu Arg Lys Ala His Ile Phe Gly Val Ser
        930                 935                 940 ttt tct atc acc cag gca atg atg tat ttt tcc tat gct ggc tgt ttc     2943
Phe Ser Ile Thr Gln Ala Met Met Tyr Phe Ser Tyr Ala Gly Cys Phe
        945                 950                 955 cgg ttt ggt gcc tac ttg gtg gca aat gag ttc atg aac ttt cag gat     2991
Arg Phe Gly Ala Tyr Leu Val Ala Asn Glu Phe Met Asn Phe Gln Asp
960                 965                 970 gtt ctt ttg gta ttc tca gct att gtc ttt ggt gcc atg gca gtg ggg     3039
Val Leu Leu Val Phe Ser Ala Ile Val Phe Gly Ala Met Ala Val Gly
                975                 980                 985                 990 cag gtc agt tca ttt gct cct gac tat gcc aaa gcc aaa gta tca gca     3087
Gln Val Ser Ser Phe Ala Pro Asp Tyr Ala Lys Ala Lys Val Ser Ala
                995                 1000                1005 gcc cac gtc atc atg atc att gaa aaa agc cct ctg att gac agc         3132
Ala His Val Ile Met Ile Ile Glu Lys Ser Pro Leu Ile Asp Ser
            1010                1015                1020 tac agc cct cac ggc ctc aag cca aat acg ttg gaa gga aat gtg         3177
Tyr Ser Pro His Gly Leu Lys Pro Asn Thr Leu Glu Gly Asn Val
            1025                1030                1035 aca ttt aat gag gtc gtg ttc aac tat ccc act cga cca gac atc         3222
Thr Phe Asn Glu Val Val Phe Asn Tyr Pro Thr Arg Pro Asp Ile
            1040                1045                1050 ccc gtg ctc cag ggg ctg agc ctc gag gtg aag aag ggc cag acg         3267
Pro Val Leu Gln Gly Leu Ser Leu Glu Val Lys Lys Gly Gln Thr
            1055                1060                1065 ctg gcc ctc gta ggt agc agt ggc tgt ggg aag agc aca gtt gtt         3312
Leu Ala Leu Val Gly Ser Ser Gly Cys Gly Lys Ser Thr Val Val
            1070                1075                1080 cag ctc cta gag cgc ttc tat gac ccc ttg gct ggt tca gtg cta         3357
Gln Leu Leu Glu Arg Phe Tyr Asp Pro Leu Ala Gly Ser Val Leu
            1085                1090                1095 att gat ggc aaa gag ata aag cac ctg aat gtc cag tgg ctc cga         3402
Ile Asp Gly Lys Glu Ile Lys His Leu Asn Val Gln Trp Leu Arg
```

```
gca cac ctg ggc atc gtg tct cag gag ccc atc ctg ttt gac tgc        3447
Ala His Leu Gly Ile Val Ser Gln Glu Pro Ile Leu Phe Asp Cys
             1115                1120                1125 agc att gcc gag aac att gcc tat gga gac aac agc cgg gtc gta        3492
Ser Ile Ala Glu Asn Ile Ala Tyr Gly Asp Asn Ser Arg Val Val
         1130                1135                1140 tca cat gaa gag att atg cag gca gcc aag gag gcc aac ata cac        3537
Ser His Glu Glu Ile Met Gln Ala Ala Lys Glu Ala Asn Ile His
         1145                1150                1155 cac ttc atc gag aca ctc cct gag aaa tac aac acc aga gta gga        3582
His Phe Ile Glu Thr Leu Pro Glu Lys Tyr Asn Thr Arg Val Gly
         1160                1165                1170 gac aaa gga acc cag ctc tct ggt ggc cag aaa cag cgc att gcc        3627
Asp Lys Gly Thr Gln Leu Ser Gly Gly Gln Lys Gln Arg Ile Ala
         1175                1180                1185 ata gct cgc gct ctt gtt aga cag cct cat att ttg ctt ttg gat        3672
Ile Ala Arg Ala Leu Val Arg Gln Pro His Ile Leu Leu Leu Asp
         1190                1195                1200 gaa gct aca tca gct ctg gat aca gaa agt gaa aag gtt gtc caa        3717
Glu Ala Thr Ser Ala Leu Asp Thr Glu Ser Glu Lys Val Val Gln
         1205                1210                1215 gaa gcc ctg gac aaa gcc aga gaa ggc cgc acc tgc att gtg atc        3762
Glu Ala Leu Asp Lys Ala Arg Glu Gly Arg Thr Cys Ile Val Ile
         1220                1225                1230 gcc cac cgc ttg tcc acc atc cag aat gca gat tta ata gtg gtg        3807
Ala His Arg Leu Ser Thr Ile Gln Asn Ala Asp Leu Ile Val Val
         1235                1240                1245 ttt cag aat ggc aaa gtc aag gag cat ggc aca cat caa cag ctg        3852
Phe Gln Asn Gly Lys Val Lys Glu His Gly Thr His Gln Gln Leu
         1250                1255                1260 ctg gct cag aaa ggc atc tat ttt tcc atg atc agt gtc cag gct        3897
Leu Ala Gln Lys Gly Ile Tyr Phe Ser Met Ile Ser Val Gln Ala
         1265                1270                1275 gga gca aag cgc tag tgaactgtgg ccatatgagc tgttaaatat ttttttaatat    3952
Gly Ala Lys Arg
         1280
ttgtgttaaa acatggcatt taatcaaagt taaaaggtga gcacttactg gaaaaactat   4012
gtagaactac ctgtttaaca tttcttgctg caactgaaga tcattccacc aagttcagag   4072
tcttcagatt ttataattaa aggaaccaaa agaaacatta tctgatggaa taaaatattg   4132
gtgttaattg cattataaaa ttatagagta attcaaagta gatttttgtta ataaattgta  4192
taatttttgt ttatatttta tttgtaactt actgctttgc tgaaagatta tagaagtggt   4252
aaaaagtact gaatgtttga ataaagtgct agctataata aaactaaact tttatatgaa   4312
aaaaa                                                               4317

<210> SEQ ID NO 2
<211> LENGTH: 1280
<212> TYPE: PRT
<213> ORGANISM: Canis familiaris

<400> SEQUENCE: 2

Met Asp Pro Glu Gly Gly Arg Lys Gly Ser Ala Glu Lys Asn Phe Trp
1               5                   10                  15

Lys Met Gly Lys Lys Ser Lys Lys Glu Lys Lys Glu Lys Lys Pro Thr
            20                  25                  30

Val Ser Thr Phe Ala Met Phe Arg Tyr Ser Asn Trp Leu Asp Arg Leu
        35                  40                  45
```

```
Tyr Met Leu Val Gly Thr Met Ala Ala Ile Ile His Gly Ala Ala Leu
     50                  55                  60

Pro Leu Met Met Leu Val Phe Gly Asn Met Thr Asp Ser Phe Ala Asn
 65                  70                  75                  80

Ala Gly Ile Ser Arg Asn Lys Thr Phe Pro Val Ile Ile Asn Glu Ser
                 85                  90                  95

Ile Thr Asn Asn Thr Gln His Phe Ile Asn His Leu Glu Glu Glu Met
                100                 105                 110

Thr Thr Tyr Ala Tyr Tyr Tyr Ser Gly Ile Gly Ala Gly Val Leu Val
            115                 120                 125

Ala Ala Tyr Ile Gln Val Ser Phe Trp Cys Leu Ala Ala Gly Arg Gln
        130                 135                 140

Ile Leu Lys Ile Arg Lys Gln Phe Phe His Ala Ile Met Arg Gln Glu
145                 150                 155                 160

Ile Gly Trp Phe Asp Val His Asp Val Gly Glu Leu Asn Thr Arg Leu
                165                 170                 175

Thr Asp Asp Val Ser Lys Ile Asn Glu Gly Ile Gly Asp Lys Val Gly
            180                 185                 190

Met Phe Phe Gln Ser Ile Ala Thr Phe Phe Thr Gly Phe Ile Val Gly
        195                 200                 205

Phe Thr Pro Gly Trp Lys Leu Thr Leu Val Ile Leu Ala Ile Ser Pro
    210                 215                 220

Val Leu Gly Leu Ser Ala Ala Ile Trp Ala Lys Ile Leu Ser Ser Phe
225                 230                 235                 240

Thr Asp Lys Glu Leu Leu Ala Tyr Ala Lys Ala Gly Ala Val Ala Glu
                245                 250                 255

Glu Val Leu Ala Ala Ile Arg Thr Val Ile Ala Phe Gly Gly Gln Lys
            260                 265                 270

Lys Glu Leu Glu Arg Tyr Asn Lys Asn Leu Glu Glu Ala Lys Arg Ile
        275                 280                 285

Gly Ile Lys Lys Ala Ile Thr Ala Asn Ile Ser Ile Gly Ala Ala Phe
    290                 295                 300

Leu Leu Ile Tyr Ala Ser Tyr Ala Leu Ala Phe Trp Tyr Gly Thr Ser
305                 310                 315                 320

Leu Val Leu Ser Ser Glu Tyr Thr Ile Gly Gln Val Leu Thr Val Phe
                325                 330                 335

Phe Ser Val Leu Ile Gly Ala Phe Ser Ile Gly Gln Ala Ser Pro Ser
            340                 345                 350

Ile Glu Ala Phe Ala Asn Ala Arg Gly Ala Ala Tyr Glu Ile Phe Lys
        355                 360                 365

Ile Ile Asp Asn Lys Pro Ser Ile Asp Ser Tyr Ser Lys Ser Gly His
    370                 375                 380

Lys Pro Asp Asn Ile Lys Gly Asn Leu Glu Phe Lys Asn Val His Phe
385                 390                 395                 400

Ser Tyr Pro Ser Arg Lys Glu Val Lys Ile Leu Lys Gly Leu Asn Leu
                405                 410                 415

Lys Val Gln Ser Gly Gln Thr Val Ala Leu Val Gly Asn Ser Gly Cys
            420                 425                 430

Gly Lys Ser Thr Thr Val Gln Leu Met Gln Arg Leu Tyr Asp Pro Thr
        435                 440                 445

Asp Gly Met Val Cys Ile Asp Gly Gln Asp Ile Arg Thr Ile Asn Val
    450                 455                 460
```

```
Arg His Leu Arg Glu Ile Thr Gly Val Val Ser Gln Glu Pro Val Leu
465                 470                 475                 480

Phe Ala Thr Thr Ile Ala Glu Asn Ile Arg Tyr Gly Arg Glu Asn Val
                485                 490                 495

Thr Met Asp Glu Ile Glu Lys Ala Val Lys Glu Ala Asn Ala Tyr Asp
            500                 505                 510

Phe Ile Met Lys Leu Pro Asn Lys Phe Asp Thr Leu Val Gly Glu Arg
        515                 520                 525

Gly Ala Arg Leu Ser Gly Gly Gln Lys Gln Arg Ile Ala Ile Ala Arg
530                 535                 540

Ala Leu Val Arg Asn Pro Lys Ile Leu Leu Leu Asp Glu Ala Thr Ser
545                 550                 555                 560

Ala Leu Asp Thr Glu Ser Glu Ala Val Val Gln Val Ala Leu Asp Lys
                565                 570                 575

Ala Arg Lys Gly Arg Thr Thr Ile Val Ile Ala His Arg Leu Ser Thr
            580                 585                 590

Val Arg Asn Ala Asp Val Ile Ala Gly Phe Asp Asp Gly Val Ile Val
        595                 600                 605

Glu Lys Gly Asn His Asp Glu Leu Met Lys Glu Lys Gly Ile Tyr Phe
    610                 615                 620

Lys Leu Val Thr Met Gln Thr Arg Gly Asn Glu Ile Glu Leu Glu Asn
625                 630                 635                 640

Ala Thr Gly Glu Ser Lys Ser Glu Ser Asp Ala Leu Glu Met Ser Pro
                645                 650                 655

Lys Asp Ser Gly Ser Ser Leu Ile Lys Arg Arg Ser Thr Arg Arg Ser
            660                 665                 670

Ile His Ala Pro Gln Gly Gln Asp Arg Lys Leu Gly Thr Lys Glu Asp
        675                 680                 685

Leu Asn Glu Asn Val Pro Ser Val Ser Phe Trp Arg Ile Leu Lys Leu
    690                 695                 700

Asn Ser Thr Glu Trp Pro Tyr Phe Val Val Gly Ile Phe Cys Ala Ile
705                 710                 715                 720

Ile Asn Gly Gly Leu Gln Pro Ala Phe Ser Ile Ile Phe Ser Arg Ile
                725                 730                 735

Ile Gly Ile Phe Thr Arg Asp Glu Asp Pro Glu Thr Lys Arg Gln Asn
            740                 745                 750

Ser Asn Met Phe Ser Val Leu Phe Leu Val Leu Gly Ile Ile Ser Phe
        755                 760                 765

Ile Thr Phe Phe Leu Gln Gly Phe Thr Phe Gly Lys Ala Gly Glu Ile
    770                 775                 780

Leu Thr Lys Arg Leu Arg Tyr Met Val Phe Arg Ser Met Leu Arg Gln
785                 790                 795                 800

Asp Val Ser Trp Phe Asp Asp Pro Lys Asn Thr Thr Gly Ala Leu Thr
                805                 810                 815

Thr Arg Leu Ala Asn Asp Ala Ala Gln Val Lys Gly Ala Ile Gly Ser
            820                 825                 830

Arg Leu Ala Val Ile Thr Gln Asn Ile Ala Asn Leu Gly Thr Gly Ile
        835                 840                 845

Ile Ile Ser Leu Ile Tyr Gly Trp Gln Leu Thr Leu Leu Leu Leu Ala
    850                 855                 860

Ile Val Pro Ile Ile Ala Ile Ala Gly Val Val Glu Met Lys Met Leu
865                 870                 875                 880

Ser Gly Gln Ala Leu Lys Asp Lys Lys Glu Leu Glu Gly Ala Gly Lys
```

-continued

```
                885                 890                 895
Ile Ala Thr Glu Ala Ile Glu Asn Phe Arg Thr Val Val Ser Leu Thr
            900                 905                 910
Arg Glu Gln Lys Phe Glu Tyr Met Tyr Ala Gln Ser Leu Gln Val Pro
            915                 920                 925
Tyr Arg Asn Ser Leu Arg Lys Ala His Ile Phe Gly Val Ser Phe Ser
            930                 935                 940
Ile Thr Gln Ala Met Met Tyr Phe Ser Tyr Ala Gly Cys Phe Arg Phe
945                 950                 955                 960
Gly Ala Tyr Leu Val Ala Asn Glu Phe Met Asn Phe Gln Asp Val Leu
            965                 970                 975
Leu Val Phe Ser Ala Ile Val Phe Gly Ala Met Ala Val Gly Gln Val
            980                 985                 990
Ser Ser Phe Ala Pro Asp Tyr Ala Lys Ala Lys Val Ser Ala Ala His
            995                 1000                1005
Val Ile Met Ile Ile Glu Lys Ser Pro Leu Ile Asp Ser Tyr Ser
    1010                1015                1020
Pro His Gly Leu Lys Pro Asn Thr Leu Glu Gly Asn Val Thr Phe
    1025                1030                1035
Asn Glu Val Val Phe Asn Tyr Pro Thr Arg Pro Asp Ile Pro Val
    1040                1045                1050
Leu Gln Gly Leu Ser Leu Glu Val Lys Lys Gly Gln Thr Leu Ala
    1055                1060                1065
Leu Val Gly Ser Ser Gly Cys Gly Lys Ser Thr Val Val Gln Leu
    1070                1075                1080
Leu Glu Arg Phe Tyr Asp Pro Leu Ala Gly Ser Val Leu Ile Asp
    1085                1090                1095
Gly Lys Glu Ile Lys His Leu Asn Val Gln Trp Leu Arg Ala His
    1100                1105                1110
Leu Gly Ile Val Ser Gln Glu Pro Ile Leu Phe Asp Cys Ser Ile
    1115                1120                1125
Ala Glu Asn Ile Ala Tyr Gly Asp Asn Ser Arg Val Val Ser His
    1130                1135                1140
Glu Glu Ile Met Gln Ala Ala Lys Glu Ala Asn Ile His His Phe
    1145                1150                1155
Ile Glu Thr Leu Pro Glu Lys Tyr Asn Thr Arg Val Gly Asp Lys
    1160                1165                1170
Gly Thr Gln Leu Ser Gly Gly Gln Lys Gln Arg Ile Ala Ile Ala
    1175                1180                1185
Arg Ala Leu Val Arg Gln Pro His Ile Leu Leu Leu Asp Glu Ala
    1190                1195                1200
Thr Ser Ala Leu Asp Thr Glu Ser Glu Lys Val Val Gln Glu Ala
    1205                1210                1215
Leu Asp Lys Ala Arg Glu Gly Arg Thr Cys Ile Val Ile Ala His
    1220                1225                1230
Arg Leu Ser Thr Ile Gln Asn Ala Asp Leu Ile Val Val Phe Gln
    1235                1240                1245
Asn Gly Lys Val Lys Glu His Gly Thr His Gln Gln Leu Leu Ala
    1250                1255                1260
Gln Lys Gly Ile Tyr Phe Ser Met Ile Ser Val Gln Ala Gly Ala
    1265                1270                1275
Lys Arg
    1280
```

<210> SEQ ID NO 3
<211> LENGTH: 20
<212> TYPE: DNA
<213> ORGANISM: synthetic oligonucleotide

<400> SEQUENCE: 3
tccggtttgg tgcctacttg                                                   20

<210> SEQ ID NO 4
<211> LENGTH: 21
<212> TYPE: DNA
<213> ORGANISM: synthetic oligonucleotide

<400> SEQUENCE: 4
tgctccttga ctttgccatt c                                                 21

<210> SEQ ID NO 5
<211> LENGTH: 22
<212> TYPE: DNA
<213> ORGANISM: synthetic oligonucleotide

<400> SEQUENCE: 5
cctcactaag cggcttcgat ac                                                22

<210> SEQ ID NO 6
<211> LENGTH: 22
<212> TYPE: DNA
<213> ORGANISM: synthetic oligonucleotide

<400> SEQUENCE: 6
aaacaggatg ggctcctgag ac                                                22

<210> SEQ ID NO 7
<211> LENGTH: 20
<212> TYPE: DNA
<213> ORGANISM: synthetic oligonucleotide

<400> SEQUENCE: 7
cagcacgttt gcaatgtttc                                                   20

<210> SEQ ID NO 8
<211> LENGTH: 22
<212> TYPE: DNA
<213> ORGANISM: synthetic oligonucleotide

<400> SEQUENCE: 8
tctggtttat gtccactctt cg                                                22

<210> SEQ ID NO 9
<211> LENGTH: 21
<212> TYPE: DNA
<213> ORGANISM: synthetic oligonucleotide

<400> SEQUENCE: 9
aggcatcccc aagcattgaa g                                                 21

<210> SEQ ID NO 10
<211> LENGTH: 20
<212> TYPE: DNA
<213> ORGANISM: synthetic oligonucleotide

```
<400> SEQUENCE: 10
tgagccgcat cattggcaag                                              20
```

METHOD OF DETECTING IVERMECTIN SENSITIVITY IN A CANINE SUBJECT BY IDENTIFYING A MUTATION IN A MDR1-ENCODING SEQUENCE

REFERENCE TO RELATED APPLICATIONS

This is a divisional of U.S. patent application Ser. No. 10/044,671, filed Jan. 10, 2002, now U.S. Pat. No. 6,790,621, issued Sep. 14, 2004, which claims the benefit of U.S. Provisional Application 60/261,578, Jan. 12, 2001, and U.S. Provisional Application 60/314,829, filed Aug. 24, 2001. All of these applications are incorporated herein by reference in their entirety.

FIELD

This disclosure relates to methods and kits for detecting a subject's sensitivity to pharmaceutical agents, particularly an animal's sensitivity to application of drugs (such as ivermectin) that interact with P-glycoprotein. It also relates to variants of the mdr1 gene, which variants impact transport of drugs that interact with the P-glycoprotein, as well as cell and whole animal systems comprising such variants and methods of using these systems.

BACKGROUND

The observation, over 100 years ago, that certain chemical dyes injected into the peripheral circulation were able to gain access to most organs but not the brain led to the concept of a blood-brain barrier. Research in the 1960's demonstrated that the anatomical basis of the blood-brain barrier is the specialized endothelial cells of brain capillaries. While it has been thought that the entry of drugs, toxins, and xenobiotics into the brain is simply a function of lipophilicity, electrical charge, and molecular weight, ongoing research demonstrates that the capillary endothelium composing the blood-brain barrier is not simply an anatomic entity. A number of active transport systems exist that selectively regulate both influx and efflux of compounds across brain capillary endothelial cells. The most important drug-efflux system of the blood-brain barrier identified to date is P-glycoprotein.

P-glycoprotein, the product of the mdr1 (multidrug resistance) gene, is a 170-kD membrane-spanning, cell-surface protein that functions as a drug-efflux pump. P-glycoprotein was first identified over 20 years ago in chemotherapeutic drug-resistant tumor cells, and is now known to be a major cause of multidrug resistance in human and veterinary cancer patients. In tumor cells, P-glycoprotein functions as an ATP-dependent efflux pump resulting in decreased intracellular drug accumulation and reduced cytotoxicity. Chemotherapeutic drugs that are substrates for P-glycoprotein include Vinca alkaloids (vincristine and vinblastine), doxorubicin and related compounds, taxanes, and epipodophyllotoxins. Alkylating agents, platinum compounds, and antimetabolites are not substrates for P-glycoprotein. Though these agents are structurally and functionally dissimilar, P-glycoprotein substrates share several other characteristics. They typically are complex, hydrophobic, amphipathic compounds that are natural products (i.e., derived from plants or micro-organisms) or analogs of natural products. A number of non-cytotoxic compounds have been identified as P-glycoprotein substrates, including steroid hormones, bilirubin, antiparasitic agents, selected antimicrobial agents, and others.

P-glycoprotein is expressed not only in tumor cells, but also in a variety of normal tissues, including renal tubular epithelium, canalicular surfaces of hepatocytes, adrenal cortical cells, colonic and intestinal epithelium, placenta, apical margins of bronchiolar epithelium, and brain capillary endothelial cells. Consistent with its function as a transport pump, the expression of P-glycoprotein in non-neoplastic tissues suggests a normal physiologic role for P-glycoprotein mediating the export of potentially toxic xenobiotics from the body. Although the normal function of P-glycoprotein in many of these tissues has not been elucidated, a great deal is known about its role in the blood-brain barrier.

Avermectins are a class of natural products with broad antiparasitic activity. Ivermectin, a semi-synthetic lactone in the avermectin family, is a drug that is used extensively in veterinary medicine to treat and control infections caused by nematode and arthropod parasites. It is also used in human medicine to treat onchocerciasis, lymphatic filariasis, and strongyloidiasis. Ivermectin induces a tonic paralysis in invertebrate organisms by potentiating glutamate-gated chloride channels, and/or gamma-amino butyric acid (GABA)-gated chloride channels (Tracy and Webster, In: *Goodman & Gilman's The Pharmacological Basis of Therapeutics, 9th edition.* Hardman et al., eds. New York: McGraw-Hill, 1996: 1009-1026, 1996) of the peripheral nervous system. In most mammals, the blood-brain barrier prevents access of ivermectin to the central nervous system, and since GABA receptors in mammals are restricted to sites within the central nervous system, mammals are generally protected from the neurologic effects of ivermectin (Fisher and Mrozik, *Annu. Rev. Pharmacol. Toxicol.* 32:537-553, 1992).

There are some specific subgroups of mice and dogs, however, that are exquisitely sensitive to the neurologic actions of ivermectin. Genetically engineered mdr1a knock-out [mdr1a (–/–)] mice are 50 to 100 times more sensitive to ivermectin-mediated neurotoxicity than wild-type mice (Schinkel et al., *Cell.* 77:491-502, 1994), and accumulate 80-90-fold higher concentrations of ivermectin in the brain than do wild-type mice. The protein product of mdr1a, called P-glycoprotein (P-gp) is a 170-kD transmembrane protein pump that is present at high concentrations in the apical membrane of brain capillary endothelial cells (Van Asperen et al., *J. Pharmaceut. Sci.* 86:881-884, 1997, 1997; Tsuji, *Therap. Drug Monitor.* 20:588-590, 1998). Substrates of P-gp include a variety of large, structurally unrelated hydrophobic compounds, including naturally occurring compounds such as ivermectin, cyclosporin, digoxin, and others. After substrates are bound by P-gp, they are actively extruded from the endothelial cell into the capillary lumen (Van Asperen et al., *J. Pharmaceut. Sci.* 86:881-884, 1997). Abrogation of P-gp results in failure of the blood-brain barrier. High concentrations of ivermectin accumulate in brain tissue from mdr1a (–/–) mice, and neurotoxicity ensues.

Approximately 25% of a population of the CF-1 mouse strain were much more sensitive to neurotoxicity produced by ivermectin than unaffected mice of the same strain (Umbenhauer et al., *Toxicol Appl. Pharmacol.* 146:88-94, 1997). Investigation into the cause of this sensitivity led to the discovery that the sensitive animals did not express P-gp in their brain endothelial cells. Furthermore, a restriction-fragment-length polymorphism in the murine mdr gene was documented that allowed prediction of sensitive animals, and an inheritance pattern following normal Mendelian genetics was observed (Umbenhauer et al., *Toxicol Appl. Pharmacol.* 146: 88-94, 1997).

In dogs, a breed-related sensitivity to ivermectin has been reported in Collies, that may affect 30 to 50% of the population (Pulliam et al., *Veter. Med.* 7:33-40, 1985; Hsu et al., *Comp. Contin. Educat. Veter. Pract.* 11:584-589, 1989, Paul et al., *Am. J. Vet. Res.* 48:685-688, 1987). In one study, 1/200th of the lethal dose of ivermectin for Beagles was lethal for Collies (Pulliam et al., *Veter. Med.* 7:33-40, 1985). Other related canine breeds believed to be affected by ivermectin sensitivity include Border Collies, Shetland Sheepdogs, Old English Sheepdogs, and Australian Shepherds (Campbell and Benz, *J. Vet. Pharmacol. Therap.* 7:1-16, 1984).

Despite numerous investigations (Vaughn, et al., *Vet. Res. Commun.* 13:47-55, 1989; Roher et al., *Vet. Res. Commun.* 14:157-165, 1990; Pulliam et al., *Veter. Med.* 7:33-40, 1985), the mechanism for ivermectin-sensitivity in Collies is unknown.

SUMMARY OF THE DISCLOSURE

The disclosure provides a mutation in the mdr1 gene, which results in production of truncated and non-functional P-gp and thereby causes sensitivity to ivermectin and other drugs that serve as P-gp substrates. With the identification of this mutation, methods are provided to determine if an individual subject is sensitive to ivermectin. Also provided are systems for examining the importance of P-gp in drug transport in whole animal and cell culture systems.

A provided embodiment is a method of detecting ivermectin sensitivity in a subject (for instance a mammal, such as a canine animal), which method includes determining whether a gene-truncation mutation in a mdr1-encoding sequence of the subject or a truncated P-pg is present in the subject. Such a gene-truncation mutation or truncation of P-gp indicates that the subject is sensitive to ivermectin. In specific examples of such methods, the gene truncation mutation is a deletion of about four base pairs at about residue 294-297 of SEQ ID NO: 1 (the canine mdr1 cDNA) or a homologous cDNA or gene.

In certain embodiments, methods provided herein are used to evaluate whether the subject can be treated safely with ivermectin or another drug that can be excluded from the brain by P-gp (such as those listed in Table 2).

In certain provided methods, the method includes determining whether the subject is homozygous or heterozygous for the gene-truncation mutation.

In specific examples of the provided methods, determining whether a gene-truncation mutation is present in the subject includes subjecting DNA or RNA from the subject to amplification using oligonucleotide primers, for instance in performing an oligonucleotide ligation assay.

In a specific embodiment provided herein, the method of detecting ivermectin sensitivity in a subject involves obtaining a test sample of DNA containing a mdr1 sequence of the subject; and determining whether the subject has the gene-truncation mutation in the mdr1 sequence, wherein the presence of the mutation indicates sensitivity to ivermectin. In certain examples of this embodiment, determining whether the subject has the mutation comprises using restriction digestion, probe hybridization, nucleic acid amplification, or nucleotide sequencing.

Further embodiments of methods provided herein involve obtaining from the subject a test sample of DNA comprising an mdr1 sequence; contacting the test sample with at least one nucleic acid probe for an mdr1 gene truncation mutation that is associated with ivermectin sensitivity, to form a hybridization sample; maintaining the hybridization sample under conditions sufficient for specific hybridization of the mdr1 sequence with the nucleic acid probe; and detecting whether the mdr1 sequence specifically hybridizes with the nucleic acid probe, wherein specific hybridization of the mdr1 sequence with the nucleic acid probe indicates ivermectin sensitivity. In specific examples of such embodiments, the probe is present on a substrate, for instance a nucleotide array.

Also provided are methods of detecting ivermectin sensitivity in a subject by determining whether truncated P-gp is present in a sample from the subject. Certain examples of such methods will involve reacting at least one P-gp molecule contained in the sample from the subject with a P-gp-specific binding agent (such as an antibody) to form a P-gp:agent complex. Such methods can further include detecting the P-gp:agent complex, for instance by Western blot assay, ELISA, or other immunoassay technique.

Also provided herein are kits for use in diagnosing ivermectin sensitivity in a subject. Such kits include at least one probe that specifically hybridizes to an mdr1 gene-truncation mutation associated with ivermectin sensitivity. In specific examples of such kits, the probe specifically hybridizes to an mdr1 gene-truncation mutation at or about residue 294-297 of SEQ ID NO: 1.

Other provided kits for use in diagnosing ivermectin sensitivity in a subject contain a P-gp-specific binding agent, such as an antibody. In specific examples of such kits, the provided agent is capable of specifically binding to truncated P-gp protein.

Also provided herein are oligonucleotides that specifically hybridize to a canine mdr1 gene-truncation mutation, for instance an oligonucleotide that hybridizes to an mdr1 gene-truncation mutation at residue 294-297.

Other embodiments are systems and methods for studying the effects of drugs (and drug candidates) on biological systems expressing a mdr1 gene truncation, such as the mdr1 gene-truncation mutation at residues 294-297. Examples of such systems include cultured cells (such as intestinal epithelial cells, brain endothelial cells (for instance, capillary endothelial cells), renal-tubular cells, hepatocytes, or neoplastic cells) isolated from a canine that naturally exhibits a gene truncation mutation in the mdr1 gene. Other examples of such systems include animal models (including for instance dogs) in which the mdr1 gene is naturally truncated, or in which such truncations have been engineered using recombinant technologies and/or cloning. Methods are also provided for using these animal models and cell systems, for instance to study drug interactions with P-gp or to examine the impact of drugs and drug candidates on biological systems. Such methods would be particularly useful in the drug approval process.

One embodiment is a method of determining a P-gp influenced biological effect of a compound on a canine cellular system, which method involves contacting a canine cell having a truncation mutation in its mdr1 gene with the compound, and comparing a characteristic (such as a genetic, physiological, chemical, or morphological characteristic) of the canine cell contacted with the compound with the characteristic of a similar canine cell that was not contacted with the compound. In such methods, a difference in the characteristic between the two cells is indicative of the P-gp influenced biological effect in the cell. In specific examples of such methods, the canine cell is a Collie cell. The truncation mutation in the mdr1 gene is in some examples a mutation at residue 294-297.

Specific types of canine cells include, but are not limited to, gastrointestinal tissue cells, renal tissue cells, nerve tissue cells, brain capillary endothelial cells, and liver tissue cells. In some methods, the canine cell is a neoplastic cell.

Also provided are methods of determining a P-gp influenced biological effect of a compound on a canine cellular system, wherein contacting the canine cell with the compound occurs in vivo in the native environment of the canine cell, for instance in a dog (such as a Collie dog).

In some examples of the provided methods, biological effects include absorption or distribution of a drug or compound, for instance a drug or compound that interacts with or is transported by P-gp.

Also provided is an animal model useful for studying a P-gp influenced biological effect of a compound, comprising a Collie identified as being homozygous or heterozygous for a truncation mutation in the mdr1 gene (for instance, a mutation at residue 294-297). Also provided are methods of using this animal model to examine the effect of compounds that interact with P-gp, for instance compounds that are transported by P-gp or that modulate its transport activity.

Compounds contemplated for use in the methods provided herein include anti-infective agents (e.g., antiviral, antibacterial, or anti-prion agents), antineoplastic agents, analgesics, neurokinin receptor antagonists, anti-emetic agents, beta-adrenergic receptor antagonists, antiepileptic agents, anti-psychotic agents, anti-depressive agents, and other drugs that act on the central nervous system.

BRIEF DESCRIPTION OF THE FIGURES

FIG. 2 is a sequence comparison of wild-type (nucleotides 275 to 708 of SEQ ID NO: 1) (top) and mutant (nucleotides 275 to 293 and 298 to 708 of SEQ ID NO: 1) (bottom) mdr1 cDNAs. As demonstrated herein, a four base pair deletion is present in the mutant cDNA. Codons in the vicinity of the deletion are indicated by brackets for both the wildtype and mutant cDNAs. Bolded letters indicate stop codons created in the mutant cDNA as a result of the frame-shift. The dashed box indicates the palindromic sequence in the vicinity of the deletion mutation.

FIG. 3 is a diagrammatic representation of the transmembrane structure of P-gp (Gottesman and Pastan, *Annu. Rev. Biochem.* 62:385-427, 1993). The mutation site (arrowhead) occurs at amino acid 75, resulting in a frame shift that generates several downstream stop codons, the first two of which occur at amino acid positions 91 and 111. Greater than 90% of the protein is predicted to be missing in dogs homozygous for the mutant allele due to the truncation.

SEQUENCE LISTING

Figure 1A:
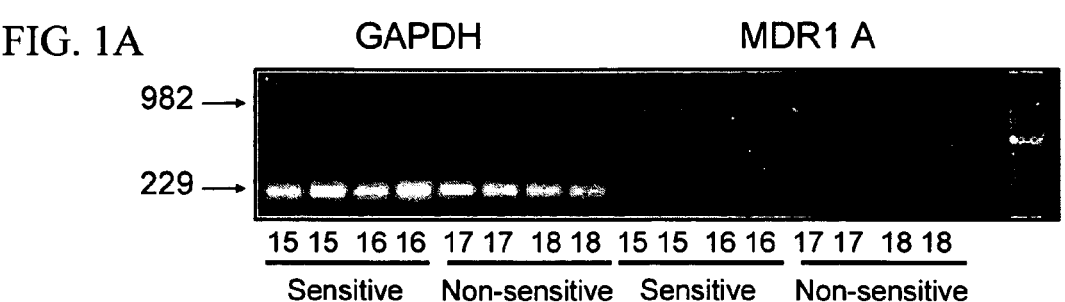
FIG. 1A is a semi-quantitative reverse transcriptase PCR analysis of mdr1 in blood samples from ivermectin-sensitive (samples 15 and 16) and non-sensitive (resistant) (samples 17 and 18) Collies. Duplicate reactions were assayed for each dog as shown using canine mdr1 and GAPDH primers. The resultant amplicons were separated by electrophoresis through an agarose gel. The arrows indicate the expected size of the mdr1 (P-gp) and GAPDH products.

The nucleic and amino acid sequences listed in the accompanying sequence listing are shown using standard letter abbreviations for nucleotide bases, and three-letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 shows the nucleotide sequence of the canine mdr1 cDNA (GenBank Accession No. AF045016), and the P-gp amino acid sequence encoded thereby.

SEQ ID NO: 2 shows the amino acid sequence of canine P-gp.

SEQ ID NOs: 3-10 show respective synthetic oligonucleotides used to primer in vitro amplification reactions of the canine mdr1 gene, as described in Example 1.

DETAILED DESCRIPTION

I. Abbreviations
   mdr multidrug resistance gene
   P-gp P-glycoprotein, protein product of the mdr1 gene II. Terms Unless otherwise noted, technical terms are used according to conventional usage. Definitions of common terms in molecular biology may be found in Benjamin Lewin, *Genes VII*, published by Oxford University Press, 2000 (ISBN 0-19-879276-X); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained herein, all technical and scientific terms used herein have the same meaning as commonly understood by one of ordinary skill in the art to which this invention belongs. The singular terms "a," "an," and "the" include plural referents unless context clearly indicates otherwise. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Identification of Truncation Mutations in mdr1, Responsible for Collie Sensitivity to Ivermectin.

There is a sub-population of Collies and dogs of related breeds that display a similar sensitivity to ivermectin. The inventors have surprisingly discovered that a deletion mutation of the mdr1 gene exists in ivermectin-sensitive Collies. The mutation produces a frame shift that generates a premature stop codon in the mdr1 gene resulting in a severely truncated, nonfunctional protein. Collies homozygous for the deletion (mutant/mutant) exhibit ivermectin sensitivity while those that are heterozygous (normal/mutant) or homozygous normal are not sensitive to ivermectin neurotoxicity. Several other breeds, including Australian shepherds, Shelties, and Old English Sheepdogs have been reported to exhibit ivermectin sensitivity; it is believed that susceptible individuals of these species may also display truncation mutations in the mdr1 gene.

The identification of the naturally occurring mdr1 truncation mutations in dogs has enabled the use of animals carrying such a mutation, and of cells derived from such animals, to study interactions of drugs (or potential drugs) with P-gp and the systemic effects of such interactions. These animal and cell-based systems are particularly useful for identifying and characterizing ways to:

(a) improve, regulate, or prevent gastrointestinal absorption of drugs;

(b) improve, regulate, or prevent brain penetration of drugs (e.g., increasing brain penetration of HIV-I drugs; drugs for treating prion diseases; antineoplastic agents; or compounds for pain or depression);

(c) improve, regulate, or prevent renal excretion of drugs;

(d) improve penetration of drugs into tumor cells;
(e) improve, regulate, or prevent biliary excretion of drugs; and
(f) improve, regulate or prevent penetration of drugs through the placenta.

These systems are also particularly useful to study the effects of functional mdr1 polymorphism(s), particularly in order to understand the effects of such polymorphisms as they may be found in additional species, including for instance humans. The systems can also be used to study the effects (drug interactions) that a highly effective, potent P-gp inhibitor would have in an intact biological system, and thus provides an excellent method for examining the large-mammal effects of drugs, for example during the drug approval and testing process.

The invention is illustrated by the following non-limiting Examples.

EXAMPLES

Example 1

Identification of a Truncation Mutation in Collie mdr1

Materials and Methods

General Procedures and Materials

Procedures used in research disclosed herein were approved by the Institutional Animal Care and Use Committee.

Blood samples (8 ml) were obtained by jugular venipuncture from each of 13 clinically healthy Collies (Wil-O-Lane Kennels, Allegan, Mich.). All Collies used in the study had previously been identified as ivermectin-sensitive or -nonsensitive by observing dogs for signs of neurotoxicosis after oral administration of 120 μg of ivermectin per kg of body weight (20 times the label dose for heartworm prevention), as previously described (Paul et al., *Amer. J. Vet. Res.* 61:482-483, 2000; Fassler et al., *J. Am. Vet. Med. Assoc.* 199:457-460, 1991). Each dog was identified by an ear tattoo and housed in a run measuring 4×8 feet with metal walls and a raised, coated, metal screen floor. Facilities exceeded the minimal requirement specified by USDA guidelines.

Seven Collies were identified as ivermectin-sensitive (4 male and 3 female) and 6 were not ivermectin-sensitive (3 male and 3 female). Two of the Collies in the study were littermates and two others were non-littermate siblings. Of the two littermates, one was sensitive to ivermectin, the other was not. Both of the non-littermate siblings were sensitive to ivermectin. Several other Collies in this study shared either the same sire or the same dam. Two of the common sires and three of the common dams were represented by offspring in both the ivermectin-sensitive and -nonsensitive groups. Additional blood samples were obtained from 4 non-Collie dogs, including 1 Beagle, 2 Golden Retrievers, and 1 Staffordshire terrier cross-bred dog.

Semiquantitative RT-PCR of Canine mdr1 Gene

Total RNA was extracted from venous blood leukocytes using TRIzol reagent (Gibco BRL). Blood leukocytes were prepared by density gradient centrifugation. For RT reactions, a GeneAmp RT PCR kit (Perlin-Elmer) was used with oligo(dT) primers. Equivalent amounts of cDNA were then amplified in separate PCR reactions using Amplitaq (Perkin Elmer) with 2.5 mM $MgCl_2$.

PCR consisted of either 20 (GAPDH) or 27 (mdr1 product A) cycles, with denaturing, annealing, and extension conditions of 95° C. (15 seconds), 60° C. (15 seconds), and 72° C. (60 seconds) in a Perkin-Elmer thermocycler (2400 GeneAmp PCR System). The number of cycles for each product was determined on the basis of kinetic studies to ensure that the amplification reaction was within the logarithmic (not plateau) range. PCR products were resolved by electrophoresis in 1% agarose gels containing ethidium bromide. Expected sizes of the GAPDH and mdr1 A band are 229 bp and 892 bp, respectively. The UV fluorescence of DNA bands was measured with an IS-1000 Digital Imaging System (Alpha Innotec). For individual dogs, the fluorescence value for the mdr1 A product is divided by the fluorescence value of the GAPDH product to allow direct comparison between dogs.

Sequencing of Canine mdr1 cDNA

Four primer pairs, amplifying four products (referred to herein as A, B, C, and D) spanning 95% of the canine mdr1 cDNA (GenBank Accession No. AF04016) were designed for sequencing experiments (see, Table 1). Using RNA from three of the sensitive Collies, cDNA was synthesized in RT reactions as described above and amplified in separate reactions. For products A, B, and C, PCR was accomplished using the conditions described above, using 35 cycles. PCR for product D consisted of 35 cycles, with denaturing, annealing, and extension conditions of 95° C. (10 seconds), 64.5° C. (15 seconds), and 72° C. (150 seconds). Optimal $MgCl_2$ concentrations were 2.5 mM for PCR products A, C, and D, and 1.5 mM for PCR product B. For initial experiments, products generated from samples of three different dogs were ligated into pGEM-T Easy (ProMega), which was then used to transform ElectroMAX DH10B *E. coli* cells by electroporation (Gene Pulser II, BioRad). Plasmid DNA was isolated (Plasmid Mini Kit, Qiagen) and sequenced by Davis Sequencing Inc. (Davis, Calif.) using dye-terminator chemistry and an automated DNA sequencer (ABI 377, PE Applied Biosystems). For all subsequent experiments, sequencing of PCR products (Davis Sequencing Inc.) following purification (Qiaquick PCR Purification Kit, Qiagen) was performed. Sequences from experimental dogs were compared to the known canine mdr1 sequence (GenBank AF 045016; SEQ ID NO: 1).

TABLE 1

Oligonucleotide primers used in this study. The combination of primer pairs used in this study provides >95% coverage of the canine mdr1 cDNA.

| Mdr1 product designation | Primer | Position | Size of PCR Product |
|---|---|---|---|
| A | Forward: 5'-TCC GGT TTG GTG CCT ACT TG[1]<br>Reverse: 5'-TGC TCC TTG ACT TTG CCA TTC[2] | 294-2961<br>3833-3814 | 892 |

TABLE 1-continued

Oligonucleotide primers used in this study. The combination
of primer pairs used in this study provides >95% coverage
of the canine mdr1 cDNA.

| Mdr1 product designation | Primer | Position | Size of PCR Product |
|---|---|---|---|
| B | Forward: 5'-CCT CAC TAA GCG GCT TCG ATA C[3]<br>Reverse: 5'-AAA CAG GAT GGG CTC CTG AGA C[4] | 2421-2441<br>3441-3420 | 1021 |
| C | Forward: 5'-CAG CAC GTT TGC AAT GTT TC[5]<br>Reverse: 5'-TCT GGT TTA TGT CCA CTC TTC G[6] | 168-189<br>1228-1208 | 1061 |
| D | Forward: 5'-AGG CAT CCC CAA GCA TTG AAG[7]<br>Reverse: 5'-TGA GCC GCA TCA TTG GCA AG[8] | 1112-1132<br>2543-2524 | 1432 |

[1]Corresponds to SEQ ID NO: 3.
[2]Corresponds to SEQ ID NO: 4.
[3]Corresponds to SEQ ID NO: 5.
[4]Corresponds to SEQ ID NO: 6.
[5]Corresponds to SEQ ID NO: 7.
[6]Corresponds to SEQ ID NO: 8.
[7]Corresponds to SEQ ID NO: 9.
[8]Corresponds to SEQ ID NO: 10.

Results

Figure 1B:
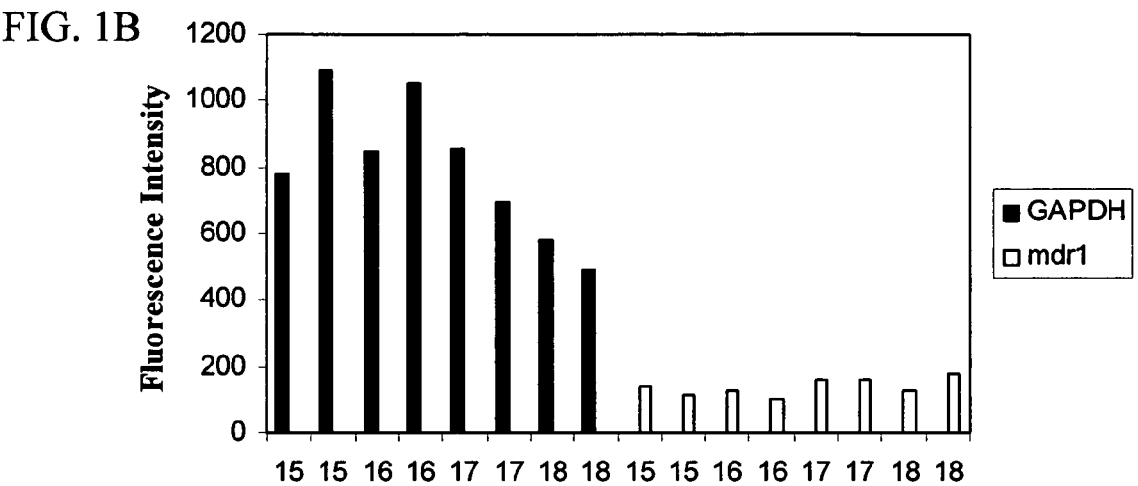
FIG. 1B is a graph, quantitating the UV fluorescence of mdr1 and GAPDH reverse transcriptase PCR products obtained by digital image analysis of the ethidium bromide-stained gel shown in FIG. 1A.

We took advantage of a well-defined population of ivermectin-sensitive and non-sensitive Collies (Paul et al., *Amer. J. Vet. Res.* 61:482-483, 2000: Fassler et al., *J. Am. Vet. Med. Assoc.* 199:457-460, 1991). Sensitive animals were designated as those that experienced clinical signs of neurologic toxicity after receiving a single, oral dose of ivermectin (120 µg/kg). Clinical signs of neurotoxicity that were evaluated include apparent depression, ataxia, mydriasis, salivation, or drooling (Paul et al., *Amer. J. Vet. Res.* 61:482-483, 2000). Semi-quantitative reverse transcriptase PCR analysis was conducted on RNA isolated from ivermectin-sensitive and non-sensitive Collies to determine if mdr1 expression is lower in sensitive Collies than in non-sensitive Collies. Amplification of a 229-bp product of the canine glyceraldehyde 3-phosphate dehydrogenase (GAPDH) gene was used as an internal standard to control for variability in reverse transcriptase and PCR reactions. FIG. 1A shows representative ethidium bromide-stained RT-PCR products of GAPDH (229 bp) and mdr1 (product A, 892 bp) from ivermectin sensitive (samples 15 and 16) and nonsensitive (samples 17 and 18) Collies. Individual UV fluorescence intensity values for GAPDH and mdr1 cDNA derived from these gels are shown in FIG. 1B. The level of mdr1 gene expression, as determined by semi-quantitative reverse transcriptase PCR, did not differ between ivermectin-sensitive and non-sensitive Collies.

A reverse transcriptase PCR strategy was used to clone mdr1 cDNA from one normal dog (beagle) and 3 ivermectin-sensitive Collies. Sequence data from the beagle mdr1 cDNA was identical to that reported for normal canine mdr1 cDNA (GenBank Accession No. AF045016). Sequence analysis of clones from the three ivermectin-sensitive Collies revealed an identical four base pair deletion within the first 10% of the transcript (FIG. 2). This deletion causes a frame-shift mutation at nucleotide 294 of the transcript, which corresponds to amino acid 75 (FIG. 3). The frame shift generates several stop codons (FIG. 3), the first of which occurs at amino acid position 91 of P-gp (GenBank Accession No. AF04016; SEQ ID NO: 2). The result is a severely truncated, nonfunctional, protein.

For all subsequent experiments, a PCR-based strategy was used for sequencing mdr1 cDNA so that heterozygosity could be readily detected. The exact four-nucleotide deletion (AGAT) was detected in all (7/7) samples from ivermectin-sensitive Collies. Furthermore, these dogs were homozygous for the deletion. Samples from all non-Collie dogs (1 Beagle, 2 Golden Retrievers, and 1 Staffordshire terrier cross-bred dog) were homozygous wild-type. Interestingly, samples from all (6/6) ivermectin non-sensitive Collies displayed a heterozygous genotype, with one strand carrying the mutant allele, and the other strand carrying the wild-type allele. It is highly unlikely that these findings are a result of chance (Fisher's Exact test, P=0.006).

Discussion

The reported data demonstrate that a frame-shift deletion of four base pairs at the 5' end of the canine mdr1 gene is associated with (and likely causes) ivermectin-sensitivity in Collies. Premature termination of P-gp synthesis as a result of the frame-shift yields a severely truncated protein that is less than one-tenth its normal size, based on the predicted amino acid sequence. P-glycoprotein's drug-efflux function is dependent upon ATP binding sites, substrate binding sites, phosphorylation sites, and multiple membrane-spanning motifs (Yoshimura et al, *J. Biol. Chem.* 264:16282-16291, 1989; Skach and Lingappa, *Cancer Res.* 54:3202-3209, 1994). Since none of these required elements are present in the truncated protein, we conclude that animals homozygous for the deletion do not express a functional form of P-gp.

The pivotal role that P-gp plays in protecting the brain from ivermectin has previously been established (Kwei et al., *Drug Metab. Dispos.* 27:581-587, 1999; Marques-Santos et al., *Pharmacol. Toxicol.* 84:125-129, 1999; Schinkel et al., *J. Clin. Invest.* 97:2517-2524, 1996; Van Asperen et al., *J Pharmaceut. Sci.* 86:881-884, 1997). Because a large number of other drugs serve as P-gp substrates, it is possible that affected Collies would also experience greater sensitivity to the neurologic effects induced by drugs other than ivermectin. Examples of P-gp substrates that might induce neurotoxicity include those listed in Table 2 (Tsuji, *Therap. Drug Monitor.* 20:588-590, 1998; Schinkel et al., *J. Clin. Invest.* 97:2517-2524, 1996).

TABLE 2

Selected Clinically Relevant Substrates of P-glycoprotein

| Antineoplastic agents | Antimicrobials and Antiparasitics | Miscellaneous |
|---|---|---|
| Vincristine* | Cefoperazone | Digoxin* |
| Vinblastine* | Tetracylines | Cyclosporine A |
| Doxorubicin* | Ivermectin* | Verapamil* |
| Mitoxantrone | | Loperamide* |
| Paclitaxel* | | Dexamethasone |
| | | Ondansetron* |

*Drugs that have potential for neurotoxicity

In mice, people, and dogs, P-gp is normally expressed in other tissues of the body in addition to brain capillaries. Consistent with its function as a transport pump, expression of P-gp occurs at sites where it might protect the animal from xenobiotics. For example, P-gp is expressed at high levels in renal proximal tubular cells, liver, small bowel, colon, and placenta (as well as brain endothelium) (Lum et al., *Pharmacother.* 13:88-109, 1993; Ginn, *Vet. Pathol.* 33:533-541, 1993). The highest levels of P-gp expression occur in tumor cells, where P-gp functions as a multidrug transporter, protecting tumor cells from a variety of chemotherapeutic drugs including anthracyclines, Vinca alkaloids, taxanes, and epipodophyllotoxins. It is believed that ivermectin-sensitive Collies would be less likely to develop multidrug resistant tumors than the general canine population, and would therefore have better chemotherapy response rates.

The specific cause of the identified mdr1 mutation is unknown. However, it has been reported that unusual DNA structures, including palindromic DNA, promote genetic instability (Lewis et al., *Ann. NY Acad. Sci.* 870:45-57, 1999). Unusual DNA structures are thought to cause DNA polymerase to pause and, consequently, can disrupt DNA replication. Mutational events are not limited to sequences located within the palindromic DNA, but can also occur in sequences in the vicinity of a palindrome. Therefore, it is interesting to note that a palindromic sequence (GGTTTTTGG (nucleotides 276-284 of SEQ ID NO: 1); FIG. 2) occurs nine bases upstream of the deletion site. Whether or not this palindromic sequence played a role in generating the four-base pair deletion in these Collies is unknown.

The inheritance pattern of ivermectin sensitivity in Collies is unknown. Results of the research described here are consistent with an autosomal recessive inheritance pattern, since only Collies that had two mutant alleles displayed the ivermectin-sensitive phenotype. However, a larger sample size will be needed to definitively determine the inheritance pattern. With many genetic diseases in people, affected individuals have many different mutations throughout the affected gene. However, in this study, all Collies had the same mutation. Because many of these animals were unrelated, it seems likely that the mutant alleles in these dogs have a common, yet-to-be-determined origin.

Example 2

Frequency of the Mutant MDR1 Allele

This Example provides methods and results from a study to determine the frequency of the mutant MDR1 allele associated with ivermectin sensitivity in a sample of Collies living in Washington and Idaho. Blood was collected from 40 Collies for RNA extraction. The RNA was reverse transcribed, and PCR performed to amplify a 1061-base pair amplicon containing the MDR1 mutation. Sequence analysis was performed to determine the genotype of each dog. Twenty-two percent of the Collies studied were homozygous for the normal allele (normal), 42% were heterozygous (carrier), and 35% were homozygous for the mutant allele (affected).

Materials and Methods

Animals—Forty clinically healthy, client-owned Collies were studied. Owner consent was obtained, and the study was approved by the Institutional Animal Care and Use Committee. Both rough-coated and smooth-coated Collies were represented. Dogs included in the sample population were those animals for which the owner was interested in determining MDR1 genotype in their pet(s). Advertising for Collies occurred primarily by announcements at the Inland Northwest Collie Club meetings and word-of-mouth. A pedigree (representing the last 4 generations) was available for eight animals.

Collection and Extraction of RNA—An 8 ml blood sample was collected from each dog for RNA isolation. Blood leukocytes were prepared by density gradient centrifugation. Total RNA was extracted from venous blood leukocytes using TRIzol reagent (Gibco BRL).

Reverse transcriptase PCR and sequencing—For reverse transcriptase reactions, a GeneAmp RT PCR kit (Perkin-Elmer) was used with oligo(dT) primers. The cDNA was then amplified (using primers as described in Example 1) in separate PCR reactions using Amplitaq (Perkin Elmer) with 2.5 mM $MgCl_2$. PCR consisted of 36 cycles, with denaturing, annealing, and extension conditions of 95° C. (10 seconds), 64° C. (15 seconds), and 72° C. (60 seconds) in a MJ Research thermocycler (PTC-200). PCR products were resolved by electrophoresis in 1% agarose gels containing ethidium bromide. Expected size of the MDR1 band was 1061 bp. PCR products were purified (Qiaquick PCR Purification Kit, Qiagen) and sequenced by Davis Sequencing Inc. (Davis, Calif.) using dye-terminator chemistry and an automated DNA sequencer (ABI 377, PE Applied Biosystems). Sequences from experimental dogs were compared to the known canine MDR1 sequence (GenBank AF 045016).

Results

The deletion mutation associated with ivermectin sensitivity in Collies was present in a large number of dogs in this study. Nine dogs (22%) were homozygous for the normal (wild-type) MDR1 sequence, 14 dogs (35%) were homozygous for the mutant allele, and 17 (42%) were heterozygous.

Analysis of the 8 pedigrees was performed and showed that four of the dogs in the study were closely related. For one pair of siblings, test results indicated that one dog was affected (homozygous mutant) and the other was heterozygous (one normal allele and one mutant allele). For another closely related pair of dogs, a dam and her daughter, test results indicated that the dam was heterozygous, and the daughter one dog was affected. However, there were two affected dogs that were not related to other dogs in the study within the four most recent generations. Furthermore, these eight dogs were unrelated (within the four most recent generations) to a sample population of Collies from Michigan that were studied previously, in which all animals were either heterozygous or homozygous for the described MDR1 mutation.

Discussion

Ivermectin sensitivity in Collies has recently been associated with homozygous expression of a deletion mutation of the MDR1 gene. P-glycoprotein, the product of the MDR1 gene, is an integral component of the blood-brain barrier. At the blood brain barrier, P-glycoprotein actively extrudes drugs from brain tissue back into capillaries, resulting in lower brain concentrations of drugs that are substrates for P-glycoprotein (Fromm, *Int J Clin Pharm Therap* 38:69-74, 2000; Kim et al., *J Clin Invest* 101:289-294, 1998; Jonker et al., *Br J Pharmacol* 127:43-50, 1999; Schinkel, *Int J Clin Pharmacol Ther* 36:9-13, 1998). In MDR1 knockout mice, lack of P-glycoprotein leads to abnormally increased accumulation of certain drugs in the brain with resultant undesired neurologic adverse effects (Schinkel, *Int J Clin Pharmacol Ther* 36:9-13, 1998). In ivermectin-sensitive Collies, this mutation consists of a 4-base-pair deletion that generates a premature stop codon, resulting in a severely truncated, non-functional protein product.

Previous investigators have estimated that up to 30-40% of Collies are sensitive to ivermectin (Pulliam et al., *Vet Med* 80:3340, 1985; Paul et al., *Am J Vet Res* 48:684-685, 1987; Rohrer and Evans, *Vet Res Commun* 14:156-165, 1990). Our study yielded similar results. In our study population, the frequency of the homozygous mutant genotype was 35%. Interestingly, in a separate sample of Collies from Michigan, all dogs carried at least one mutant allele. From the pedigrees available, 8/40 from this sample and 15/15 from the Michigan sample, none of the Washington/Idaho dogs were related to the Michigan dogs within the four most recent generations. Collectively, these results suggest that the MDR1 mutation associated with ivermectin sensitivity is widely dispersed in the Collie population.

Sporadic descriptions of ivermectin sensitivity have been reported in a few other breeds including Shetland sheepdogs, Australian shepherds, and Old English sheepdogs (Hadrick et al., *JAVMA* 206:1147-1150, 1995; Paradis, *Compend Cont Ed Pract Vet* 20:193-200, 1998; Hsu et al., *Compend Cont Ed Pract Vet* 11:584-588, 1989). Whether or not these breeds share the same MDR1 mutation as Collies is unknown. In people, several different MDR1 mutations have been described, so it is reasonable to assume that other breeds may not share the same MDR1 genotype as do Collies (Cascorbi et al., *Clin Pharmacol Ther* 69:169-174, 2001; Kerb et al., *Pharmacogenomics* 1:51-64, 2001).

Determination of the genotype of Collies is important clinically for several reasons. First, ivermectin is not the only clinically relevant substrate for P-gp that can cause neurotoxicity. The over-the-counter antidiarrheal agent loperamide has been reported to cause neurotoxicity in Collies at doses routinely used in other breeds (Hugnet et al., *Vet Hum Toxicol* 38:31-33, 1996). Loperamide, like ivermectin, is generally excluded from entering brain tissue in high concentrations by the actions of P-gp. In affected Collies, loperamide achieves high concentrations in brain tissue causing neurologic toxicity. In support of this fact, one of the Collies in the present study was treated with an appropriate dose of loperamide as a puppy and developed severe (nearly fatal) neurologic toxicity. The dog tested homozygous for the mutant allele. Other drugs that are substrates for P-gp and that can cause neurotoxicity in affected Collies include vincristine, vinblastine, ondansetron, and potentially moxidectin.

There are other, non-neurologic, implications for Collies with the MDR1 mutation described. P-glycoprotein is normally also expressed at the luminal border of the intestinal tract (Liu and Hu, *Clin Chem Lab Med* 38:877-881, 2000), where it functions as an "anti-absorption" mechanism for a number of drugs, including digoxin, cyclosporin A, dexamethasone, antiviral drugs and others (Wacher et al., *Advanced Drug Delivery Rev* 46:89-102, 2001). In affected Collies, oral bioavailability of these drugs is likely to be greater than in unaffected dogs. This would result in higher plasma concentrations and a higher likelihood of adverse drug reactions in affected Collies.

It is likely that a high percentage of Collies presented to veterinarians for treatment are affected by the MDR1 mutation described in this report. It is important that veterinarians consider this factor when selecting pharmacological therapy for Collies. Furthermore, an adverse drug reaction involving neurologic toxicity should be considered for Collies exhibiting abnormal CNS signs.

Example 3

Other mdr1 Truncations

With the provision herein of the correlation between a canine mdr1 gene truncation and ivermectin sensitivity, the isolation and identification of additional mdr1 truncations, and similar truncations in other canine species, is enabled. Conventional methods for the identification of genetic polymorphisms in a population can be used to identify such additional polymorphisms.

For instance, existing populations (e.g., Collie or other populations) are assessed for ivermectin sensitivity (or sensitivity to other drugs that interact with P-gp), and a subset of individuals within the population (such as those subjects known to be prone to neurotoxicosis, or related individuals) are genotyped as relates to an mdr1 sequence. These mdr1 sequences are then compared to a reference mdr1 sequence, such as the frame-shift truncation allele described herein, to determine the presence of one or more variant nucleotide positions. After variant nucleotides are identified, statistical analysis of the population can be used to determine whether these variants are correlated with sensitivity to ivermectin or other drug treatment.

Alternatively, the P-gp protein itself can be analyzed in such subjects, to determine the presence and/or level and/or size of the protein.

Example 4

Clinical Uses of mdr1 Polymorphisms

To perform a diagnostic test for the presence or absence of a truncation mutation (e.g., a deletion, frameshift, point mutation, or other change that results in a truncated protein product) in an mdr1 sequence of an individual, a suitable genomic DNA-containing sample from a subject is obtained and the DNA extracted using conventional techniques. Most typically, a blood sample, a buccal swab, a hair follicle preparation, or a nasal aspirate is used as a source of cells to provide the DNA sample. The extracted DNA is then subjected to amplification, for example according to standard procedures. The allele of the truncation mutation is determined by conventional methods including manual and automated fluorescent DNA sequencing, primer extension methods (Nikiforov, et al., *Nucl. Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single-strand conformation polymorphism (SSCP), denaturing gradient gel electrophoresis (DGGE), Taq-Man, oligonucleotide hybridization, and the like. Also, see the following U.S. Patents for descriptions of methods or applications of polymorphism analysis to disease prediction and/or diagnosis: U.S. Pat. Nos. 4,666,828; 4,801,531; 5,110,920; 5,268,267; and 5,387,506.

The markers of ivermectin sensitivity disclosed herein can be utilized for the detection of, and differentiation of, individuals who are homozygous and heterozygous for the truncation mutation polymorphism(s). The value of identifying individuals who carry a sensitive allele of mdr1 (i.e., individuals who are heterozygous or homozygous for an allele that contains a "sensitive" mdr1 polymorphism, such as the truncation described herein) is that therapy for these individuals can then be initiated or customized (e.g., through avoiding ivernectin or other drugs usually kept from crossing the blood-brain barrier by P-gp) to reduce the occurrence of neurotoxicity in these individuals. Likewise, the presence of the allele will assist breeders in breeding programs, either to avoid introducing a sensitive allele into a breeding population, or by selectively avoiding animals carrying such an allele. Information regarding an animal's mdr1 allele status (sensitive, resistant, or heterozygous) could for instance be tested early in the life of the individual, and included on a license, medical record, pedigree, and so forth.

Example 5

Polymorphism Gene Probes and Markers

Sequences surrounding and overlapping truncation polymorphisms in the mdr1 gene can be useful for a number of gene mapping, targeting, and detection procedures. For example, genetic probes can be readily prepared for hybridization and detection of the described truncation polymorphism. Such probe sequences may be greater than about 12 or more oligonucleotides in length and possess sufficient complementarity to distinguish between a wild-type sequence and a sequence in which four nucleotides (e.g., nucleotides corresponding to positions 294-297 of SEQ ID NO: 1) have been lost.

Similarly, sequences surrounding and overlapping the specifically disclosed truncation polymorphism (or other polymorphisms found in accordance with the present teachings) can be utilized in allele-specific hybridization procedures. A similar approach can be adopted to detect other mdr1 polymorphisms, such as truncations.

Sequence surrounding and overlapping a mdr1 polymorphism, or any portion or subset thereof that allows one to identify the polymorphism, are highly useful. Thus, another embodiment provides a genetic marker predictive of the herein-disclosed frame-shift truncation polymorphism of mdr1, comprising a partial sequence of the canine genome including at least about 10 contiguous nucleotide residues including residues 294-297 of SEQ ID NO: 1, or specifically not including these four residues but still including the surrounding residues (in other words, specific for a deletion mutant in these four residues). Examples of such oligonucleotides include the following nucleotide sequence: AAACATGACAGATAGCTTTGCAAAT (corresponding to residues 284-309 of SEQ ID NO: 1), and sequences complementary therewith, wherein the underlined four nucleotides can be left out to create an oligonucleotide specific for the disclosed gene truncation mutation.

Example 6

Detecting mdr1 Mutations

The truncation mutation at nucleotide residue 294-297 of SEQ ID NO: 1 of canine mdr1 (the first position of which encodes amino acid residue 75 of P-gp, SEQ ID NO: 2) can be detected by a variety of techniques. These techniques include allele-specific oligonucleotide hybridization (ASOH) (Stoneking et al., *Am. J. Hum. Genet.* 48:370-382, 1991), which involves hybridization of oligonucleotide probes to the sequence, stringent washing, and signal detection. Other applicable methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified (e.g., by PCR) using one biotinylated primer. The biotinylated product strand is bound to a streptavidin-coated microtiter plate well (or other suitable surface), and the non-biotinylated strand is rinsed away with alkali wash solution. An oligonucleotide probe, specific for one allele (e.g., the wild-type allele), is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the polymorphisms in DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

Example 7

Expression of P-gp

The expression and purification of proteins, such as the P-gp, can be performed using standard laboratory techniques. After expression, purified P-gp may be used for functional analyses, antibody production, diagnostics, and patient therapy. Furthermore, the DNA sequence of the mdr1 cDNA can be manipulated in studies to understand the expression of the gene and the function of its product. Mutant forms of the canine mdr1 gene may be isolated based upon information contained herein, and may be studied in order to detect alteration in expression patterns in terms of relative quantities, tissue specificity, molecular weight, stability, and functional properties of the encoded mutant P-gp protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to P-gp proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al (*In Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (*In Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (*In Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). P-gp fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous mdr1 cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). The level of expression of the cDNA can be manipulated with this type of vector, either by using promoters that have different activities. For example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one also can produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and van der Eb, *Virology* 52:456-467, 1973) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr.* 7:235, 1985), adenoviruses (Ahmad et al., *J. Virol.* 57:267, 1986), or Herpes virus (Spaete et al., *Cell* 30:295, 1982). P-gp encoding sequences also can be delivered to target cells in vitro via non-infectious systems, for instance liposomes.

These eukaryotic expression systems can be used for studies of P-gp encoding nucleic acids and mutant forms of these molecules, the P-gp protein and mutant forms of this protein.

Using the above techniques, the expression vectors containing the mdr1 gene sequence or cDNA, or fragments or variants or mutants thereof, can be introduced into canine cells, mammalian cells from other species, or non-mammalian cells as desired. The choice of cell is determined by the purpose of the introduction. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or canine fibroblasts or lymphoblasts may be used.

This disclosure thus encompasses recombinant vectors that comprise all or part of the mdr1 gene or cDNA sequences, for expression in a suitable host. The mdr1 DNA is operatively linked in the vector to an expression control sequence in the recombinant DNA molecule so that the P-gp polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with a vector described herein, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human or canine tissue cells.

It is appreciated that, for mutant or variant mdr1 DNA sequences, similar systems are employed to express and produce the mutant product. In addition, fragments of the P-gp protein can be expressed essentially as detailed above. Such fragments include individual P-gp protein domains or subdomains, as well as shorter fragments such as peptides. P-gp protein fragments having therapeutic properties may be expressed in this manner also.

Example 8

Production of P-gp Protein Specific Binding Agents

Monoclonal or polyclonal antibodies may be produced to either the normal P-gp or mutant forms (e.g., truncations) of this protein. Optimally, antibodies raised against these proteins or peptides would specifically detect the protein or peptide with which the antibodies are generated. That is, an antibody generated to the P-gp or a fragment thereof would recognize and bind the P-gp and would not substantially recognize or bind to other proteins found in human cells.

The determination that an antibody specifically detects P-gp is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects P-gp by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect P-gp will, by this technique, be shown to bind to P-gp band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-P-gp binding.

Substantially pure P-gp or protein fragments (peptides) suitable for use as an immunogen may be isolated from transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared using one of the following techniques.

A. Monoclonal Antibody Production by Hybridoma Fusion

Monoclonal antibody to epitopes of P-gp, or specifically to the truncation protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 7), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/mil of serum (about 12 μM). Affinity of the antisera for the antigen is determined by preparing competitive binding curves, as described, for example, by Fisher (*Manual of Clinical Immunology*, Ch. 42, 1980).

C. Antibodies Raised against Synthetic Peptides

A third approach to raising antibodies against P-gp or peptides is to use one or more synthetic peptides synthesized on a commercially available peptide synthesizer based upon the predicted amino acid sequence of P-gp or peptide. Polyclonal antibodies can be generated by injecting these peptides into, for instance, rabbits.

D. Antibodies Raised by Injection of P-gp Encoding Sequence

Antibodies may be raised against P-gp proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the P-gp encoding sequence (mdr1 gene or cDNA, for instance) under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of P-gp.

For administration to specific animal subjects (such as human or canine individuals), antibodies, e.g., P-gp specific monoclonal antibodies, can be adapted to be more effective in the target organism by methods known in the art. By way of example, antibodies with a desired binding specificity can be commercially humanized (Scotgene, Scotland, UK; Oxford Molecular, Palo Alto, Calif.).

Example 9

Protein-Based Detection

An alternative method of detecting sensitivity to ivermectin and related drugs (those that are kept from crossing the blood-brain barrier by P-gp) is to examine the level or molecular weight (apparent size, e.g., on after SDS-PAGE with or without immunodetection) of P-gp in the cells of an individual. These diagnostic tools would be useful for detecting reduced levels of P-gp that result from, for example, mutations in the promoter regions of the mdr1 gene or mutations within the coding region of the gene that produced truncated, non-functional or unstable polypeptides, as well as from deletions of a portion of or the entire mdr1 gene.

Localization and/or coordinated mdr1 expression (temporally or spatially) can also be examined using known techniques, such as isolation and comparison of P-gp from cell or tissue specific, or time specific, samples. The determination of reduced or increased P-gp levels, in comparison to such expression in a control cell (e.g., normal, as in taken from an individual not exhibiting sensitivity to ivermectin or another neurotoxin), would be an alternative or supplemental approach to the direct determination of mdr1 gene mutation (e.g., truncation mutation) status by the methods outlined above and equivalents.

The availability of antibodies specific to P-gp will facilitate the detection, measurement (e.g., molecular weight determination) and quantitation of cellular P-gp by one of a number of immunoassay methods which are well known in the art and are presented in Harlow and Lane (*Antibodies, A Laboratory Manual*, CSHL, New York, 1988). Methods of constructing such antibodies are discussed above, in Example 8.

Any standard immunoassay format (e.g., ELISA, Western blot, or RIA assay) can be used to measure P-gp polypeptide or protein levels; comparison is to wild-type (normal) P-gp, and an alteration in P-gp polypeptide may be indicative of an abnormal biological condition regarding resistance to potential neurotoxins, such as ivermectin. Immunohistochemical techniques may also be utilized for P-gp polypeptide or protein detection. For example, a tissue sample may be obtained from a subject, and a section stained for the presence of P-gp using a P-gp specific binding agent (e.g., anti-P-gp antibody) and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying or determining the estimated molecular weight of P-gp, a biological sample of the subject (which can be any animal, for instance a dog or a human), which sample includes cellular proteins, is required. Such a biological sample may be obtained from body cells, such as those present in peripheral blood, urine, saliva, tissue biopsy, amniocentesis samples, surgical specimens and autopsy material. Quantitation and/or measurement of P-gp can be achieved by immunoassay and compared to level and apparent size of the protein found in control cells (e.g., healthy, as in from an individual known not to have ivermectin sensitivity). A significant (e.g., 10% or greater) reduction in the amount of P-gp in the cells of a test subject compared to the amount of P-gp found in normal cells, or a substantial reduction in the apparent molecular weight of the P-gp (e.g., as would be apparent with a truncation mutation) could be taken as an indication that the subject may have deletions or mutations in the mdr1 gene. Deletion and/or mutation of or within the mdr1-encoding sequence, and substantial underexpression of P-gp, may be indicative of altered sensitivity to ivermectin and other drugs that are usually kept from crossing the blood-brain barrier by P-gp.

Merely by way of example, canine P-gp can be analyzed as described in Mealey et al., *Cancer Letters* 126:187-192, 1998. For instance, immunoblotting has been carried out using the following procedure:

Cells were harvested by trypsinization, washed with DPBS and solubilized in tumor solubilization buffer (TSB, 50 mM Tris-HCl (pH 6.8), 50 mM KCl, 5 mM EGTA, 5 mM $MgCl_2$, 2% CHAPS, 0.11 mM leupeptin, 0.2 mM phenylmethylsulfonylfluoride and 10 mM dithiothreitol). Insoluble complexes were cleared by a 5-minute spin (1500 revolutions/minute) and the soluble protein was collected for quantitation using a modified Lowry technique (Lowry, *J. Biol. Chem.* 193:265-275, 1951).

Protein samples were separated by SDS-PAGE and electroblotted onto an Immobilon-P™ membrane (Millipore, Bedford, Mass.). Membranes were washed with blotto buffer (50 mM Tris-HCl, 2 mM $CaCl_2$, 80 mM NaCl, 5% non-fat dry milk, 0.2% Nonidet P40 and 0.03% sodium azide) for one hour at 25° C. and then incubated (25° C. for 16 hours) with a murine anti-human P-glycoprotein monoclonal antibody (C219; Signet, Dedham, Mass.). Actin was subsequently detected using a monoclonal anti-actin antibody (ICN Immunobiologicals, Costa Mesa, Calif.). Membranes were washed in fresh blotto (non-fat milk) buffer and incubated with the appropriate alkaline phosphatase-labeled secondary antibody. Membranes were washed with buffer A (50 mM Tris-HCl, 2 mM $CaCl_2$ and 80 mM NaCl) and developed using nitroblue tetrazolium and 5-bromo-4-chloro-3-indolyl phosphate with an alkaline-phosphatase conjugate substrate kit (BioRad, Hercules, Calif.). The color reaction was terminated by washing in distilled water. The resulting bands were scanned with a Visage 110 camera-based densitometer (Bio-Image, Ann Arbor, Minn.) and analyzed using whole band software. Integrated intensity signals for P-glycoprotein can be normalized to those of a protein the level of which is not expected to change under the experimental conditions.

Example 10

Differentiation of Individuals Homozygous Versus Heterozygous for the Polymorphism(s)

As will be appreciated, the oligonucleotide ligation assay (OLA), as described at Nickerson et al (*Proc. Natl. Acad. Sci. USA* 87:8923-8927, 1990), allows the differentiation between individuals who are homozygous versus heterozygous for the herein-described frame-shift truncation mutation in mdr1. This feature allows one to rapidly and easily determine whether an individual is homozygous for at least a neurotoxin sensitivity-linked polymorphism, which condition can result in neurotoxicosis and possible death when an individual is administered an otherwise safe drug dosage. Alternatively, OLA can be used to determine whether a subject is homozygous for either of these polymorphisms.

As an example of the OLA assay, when carried out in microtiter plates, one well is used for the determination of the presence of the mdr1 allele that contains the herein-described frame-shift truncation mutation, and a second well is used for the determination of the presence of the mdr1 wild-type allele. Thus, the results for an individual who is heterozygous for the polymorphism will show a signal in each of the "truncated" and wild-type wells, and an individual who is homozygous for one allele or the other will show a signal only in the corresponding well.

Likewise, truncation itself can be used to detect heterogeneity in the P-gp protein. Because truncation leads to production of a shorter (and therefore "lighter") protein product, Western analysis can be used to distinguish between heterozygous and homozygous individuals, as well as between homozygous truncated (and therefore sensitive) and wild-type (resistant) individuals.

Example 11

Kits

Kits are provided which contain the necessary reagents for determining the presence or absence of polymorphism(s) in a P-gp-encoding sequence, such as probes or primers specific for the mdr1 gene. Such kits can be used with the methods described herein to determine whether an individual is likely to be sensitive to ivermectin and other drugs that are usually kept from crossing the blood-brain barrier by P-gp (such as those listed in Table II).

The provided kits may also include written instructions. The instructions can provide calibration curves or charts to compare with the determined (e.g., experimentally measured) values.

Kits are also provided to determine altered (e.g., lowered) expression of mRNA (i.e., containing probes) or P-gp protein (i.e., containing antibodies or other P-gp-specific binding agents), as well as truncated P-gp.

A. Kits for Detecting mdr1 Nucleic Acid Mutations

The oligonucleotide probes and primers disclosed herein can be supplied in the form of a kit, for use in detection of ivermectin sensitivity in a subject. In such a kit, an appropriate amount of one or more of the oligonucleotides is provided in one or more containers. The oligonucleotides may be provided suspended in an aqueous or other solution, or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of an mdr1 polymorphism can be added to the individual tubes and amplification or other laboratory manipulation carried out directly.

The amount of each oligonucleotide supplied in the kit can be any appropriate amount, depending for instance on the market to which the product is directed. For instance, if the kit is adapted for research or clinical use, the amount of each oligonucleotide primer provided would likely be an amount sufficient to prime several in vitro nucleic acid amplification reactions. Those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

A kit may include more than two primers, in order to facilitate the in vitro amplification of mdr1 sequences, for instance the mdr1 gene or the 5'- or 3'-flanking region thereof.

In some embodiments, kits may also include the reagents necessary to carry out nucleotide amplification reactions, including, for instance, DNA sample-preparation reagents, appropriate buffers (e.g., polymerase buffer), salts (e.g., magnesium chloride), and deoxyribonucleotides (dNTPs).

Kits may include either labeled or unlabeled oligonucleotide probes for use in detection of mdr1 polymorphism(s). In certain embodiments, these probes will be specific for a potential polymorphism that may be present in the target sequence. The appropriate sequences for such a probe will be any sequence that includes all or part of the identified polymorphic site, particularly nucleotide positions 294 through 297 of the canine mdr1 gene, such that the sequence the probe is complementary to the truncation polymorphic site and a portion of the surrounding mdr1 sequence. An oligonucleotide including the sequence AAACATGAC AGATAGCTTTGCAAAT (corresponding to residues 284-309 of SEQ ID NO: 1) exemplifies such a sequence, and a probe useful for disclosed methods could comprise this sequence. Alternatively, an example of a probe specific for detecting the ivermectin sensitivity allele of mdr1 may include the following sequence: AAACATGACAGTTTG-CAAAT (also corresponding to residues 284-309 of SEQ ID NO: 1, but with residues 294-297 removed).

It also may be advantageous to provide in the kit one or more control sequences for use in the amplification reactions. The design of appropriate positive and negative control sequences is well known to one of ordinary skill in the appropriate art.

B. Kits for Detection of mdr1 mRNA

Kits similar to those disclosed above for the detection of mdr1 polymorphisms directly can be used to detect mdr1 mRNA expression, such as over- or under-expression or expression of a truncated form. Such kits include an appropriate amount of one or more oligonucleotide primers for use in, for instance, reverse transcription nucleic acid amplification reactions (e.g., RT-PCR), similarly to those oligonucleotides described above with art-obvious modifications for use with RNA amplification.

In some embodiments, kits for detection of altered expression of mdr1 mRNA may also include some or all of the reagents necessary to carry out RT-PCR or other in vitro amplification reactions, for instance, RNA sample preparation reagents (including e.g., an RNase inhibitor), appropriate buffers (e.g., polymerase buffer), salts (e.g., magnesium chloride), and deoxyribonucleotides (dNTPs). Written instructions also may be included.

Such kits may in addition include either labeled or unlabeled oligonucleotide probe(s) for use in detection of the in vitro amplified target sequences. The appropriate sequences for such a probe will be any sequence that falls between the annealing sites of the two provided oligonucleotide primers, such that the sequence the probe is complementary to is amplified during the in vitro amplification reaction. In certain embodiments, these probes will be specific for a potential polymorphism that may be present in the amplified target sequences.

It also may be advantageous to provide in the kit one or more control sequences for use in the RT-PCR reactions. The design of appropriate positive and negative control sequences is well known to one of ordinary skill in the appropriate art.

Alternatively, kits may be provided with the necessary reagents to carry out quantitative or semi-quantitative Northern analysis of mdr1 mRNA. Such kits include, for instance, at least one mdr1-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential polymorphism (e.g., a truncation mutation) that may be present in the target sequences.

C. Kits For Detection of P-gp Expression

Kits for the detection of P-gp protein expression (such as over- or under-expression), and particularly changes in the apparent molecular weight of expressed P-gp, are also encompassed herein. Such kits may include at least one target-protein-specific binding agent (e.g., a polyclonal or monoclonal antibody or antibody fragment that specifically recognizes P-gp) and may include at least one control (such as a determined amount of P-gp, with a defined molecular weight or apparent size, or a sample containing a determined amount of P-gp). The P-gp-protein-specific binding agent and control may be contained in separate containers.

P-gp expression detection kits may also include a means for detecting P-gp:binding agent complexes, for instance the agent may be detectably labeled. If the binding agent is not labeled, it may be detected by second antibodies or protein A for example, which components may also be provided in some kits in one or more separate containers. Such detection techniques are known.

Additional components in specific kits may include instructions for carrying out the assay. Instructions will allow the tester to determine whether P-gp expression levels are elevated, and/or whether the expressed P-gp has an altered molecular weight compared to wild-type P-gp. Reaction vessels and auxiliary reagents such as chromogens, buffers, enzymes, etc. may also be included in the kits.

D. Kits for Detection of Homozygous versus Heterozygous Allelism

Also provided are kits that allow differentiation between individuals who are homozygous versus heterozygous for a truncation mutation in the mdr1 gene. Certain examples of such kits provide the materials for performing oligonucleotide ligation assays (OLA), as described by Nickerson et al., *Proc. Natl. Acad. Sci. USA* 87:8923-8927, 1990. In specific embodiments, these kits contain one or more microtiter plate assays, designed to detect polymorphism(s) in the mdr1 sequence of a subject, as described herein.

In other examples of such kits, materials are provided for examining the size of the P-gp expressed by an individual, for instance components for carrying out a Western analysis or other immunological assay.

Additional components in some of these kits may include instructions for carrying out the assay. Instructions will allow the tester to determine whether an mdr1 truncation mutation allele is homozygous or heterozygous, either through examination of nucleic acid molecules or protein. Reaction vessels and auxiliary reagents such as chromogens, buffers, enzymes, etc. may also be included in the kits.

It may also be advantageous to provide in the kit one or more control sequences for use in the OLA or immunoassay reactions. The design of appropriate positive and negative control molecules is well known to one of ordinary skill in the appropriate art.

Example 12

Animal Model

A large number of P-gp substrates are routinely prescribed in humans, including HIV-1 protease inhibitors and many chemotherapeutic agents. Animals (e.g., Collies) possessing a polymorphism of the mdr1 gene, for instance, the truncation mutation described herein, can serve as a useful model for studying the effects of P-glycoprotein substrates on humans with mdr1 polymorphisms. In addition, these animals can serve as models for studying the effects of compounds that interact with P-gp. They are also useful to study pharmacologic inhibition of P-gp, for instance in order to identify or characterize modulators of P-gp transport activity that may be useful to increase (or decrease, or regulate) drug absorption in or distribution to one or more tissues in a subject.

Use of the animals identified herein (particularly Collies) possessing a naturally-occurring polymorphism of the mdr1 gene avoids confounding effects attributable to producing mdr1 mutations through genetic engineering, and is expected to result in better acceptance as a research model by both the research community and society.

Using methods described herein, individual animals are identified as being heterozygous or homozygous for an mdr1 truncation, and these animals are used as subjects for animal model studies. In specific examples, a drug of interest (or drug candidate or other compound or mixture thereof) is administered to Collies possessing a polymorphism of MDR-1, and the effects are monitored systemically, for instance, or in particular tissues. Routes of administration include but are not limited to oral and parenteral routes, such as intravenous (iv), intraperitoneal (ip), rectal, topical, ophthalmic, nasal, and transdermal.

Effective doses of the compound(s) of interest can be determined by one of ordinary skill in the art, and may be tailored to the specific experiments being run. In some embodiments, the compound is administered with a goal of achieving tissue concentrations that are at least as high as the $IC_{50}$ of the compounds(s) tested. An example of such a dosage range is 0.1 to 200 mg/kg body weight. The specific dose level and frequency of dosage for any particular subject may be varied and will depend upon a variety of factors, including the activity of the specific compound, the metabolic stability and length of action of that compound, the age, body weight, mode and time of administration, and the rate of excretion of the compound.

Systemic effects of the compound of interest can be monitored in the animal following its administration. For example, neurological symptoms linked to a drug passing across one or more cellular membranes via P-gp can include salivation, vomiting, confusion, ataxia, tremors, seizure-like activity, recumbency, non-responsiveness, and coma. Alternatively, drug or other compound levels in the blood, or biochemical changes in the gastrointestinal tract, kidneys, nervous system, liver, tumor cells, or other tissues, can be monitored.

The animal model can also be used to identify and/or characterize test compounds known to, or expected to, modulate the activity of P-gp. In examples of such methods, the animals are treated (e.g., concurrently or sequentially) with both the test compound and a compound known to be transported by P-gp (the effector molecule). The animals are then monitored to detect one or more effects caused by the effector compound, and the level of effect can be compared to animals that were not treated with the test compound (or which received a different treatment regimen). Depending on the effector molecule used, different biological characteristics of the animal, or a tissue or cell within the animal, can be monitored to determine whether (and to what extent) the test compound influences P-gp interaction with the effector. Depending on whether the test molecule increases or decreases P-gp transport of the effector, the test molecule is identified as an agonist or antagonist of P-gp activity and can be selected for further characterization.

Example 13

Cultured Cells

Cells or tissues from animals (e.g., Collies) possessing a polymorphism of the mdr1 gene, for instance, the truncation mutation described herein, also can serve as useful model systems for studying the effects of P-gp interacting molecules. In addition, cells and tissues from animals possessing a polymorphism of the mdr1 gene can serve as models for studying pharmacologic inhibition, stimulation, and/or regulation of P-gp.

In some examples of such cell-based models, cells from an animal carrying an mdr1 truncation as described herein are transformed (stably or transiently) with an mdr1 construct, for instance which comprises known (e.g., engineered) or unknown mutations (e.g., point mutations such as a naturally occurring polymorphism, for instance polymorphisms identified in human mdr1). Such cellular expression systems enable examination of the activity of the mutant mdr1 construct in a defined large mammal background.

P-gp is expressed in many tissues throughout the mammalian body, including the epithelium of the gastrointestinal tract, renal-tubular epithelium, brain capillary endothelial cells, biliary tubular epithelial cells, and at the plasma membrane in many tumor cells. In some examples, cells used for the in vitro cell system are selected from a specific tissue or cell type, so that tissue or cell specific effects of P-gp transport can be studied. In carrying out such methods, specific tissues are isolated from canines (e.g., Collies) possessing a polymorphism of the mdr1 gene, such as the truncation described herein. Though methods are widely known for isolating cells and tissues of specific types, the following procedures are provided as specific examples and can be used to isolate specific cells from canine samples:

(a) Canine intestinal epithelial cells can be isolated and cultured as described in Koop and Buchan, *Gastroenterology* 102: 28-34, 1992.

(b) Canine brain microvessel endothelial cells can be isolated and cultured as described in Drewes et al., *Brain Research Bulletin* 21: 771-776, 1988.

(c) Canine renal-tubular cells can be isolated and cultured as described in Hamada et al., *Nephron.* 68: 104-111, 1994.

(d) Canine hepatocytes can be isolated and cultured as described in Lu and Li, *Chem. Biol. Interact.* 143: 271-281, 2001, Amacher and Martin, *Fundam. Appl Toxicol.* 40:256-263, 1997, or Placidi et al., *Drug Metab. Dispos.* 25: 94-99, 1997.

(e) Neoplasms can be induced using techniques well known in the art, including but not limited to the use of chemical carcinogens, viruses, and radiation exposure. Alternatively, naturally occurring tumors can also serve as a source for cancerous cells. Tumor cells can then be cultured as described in Lehr et al., *Anticancer Res.* 18(6A): 4483-4488, 1998.

The cell-based model can also be used to identify and/or characterize test compounds known to, or expected to, modulate the activity of P-gp. In examples of such methods, the cells are contacted (e.g., concurrently or sequentially) with both the test compound and a compound known to be transported by P-gp (the effector molecule). The cells are then monitored to detect one or more effects caused by the effector compound, and the level of effect can be compared to animals that were not treated with the test compound (or which received a different treatment regimen). Depending on the effector molecule used, different biological characteristics of the cells can be monitored to determine whether (and to what extent) the test compound influences P-gp interaction with the effector. Depending on whether the test molecule increases or decreases P-gp transport of the effector, the test molecule is identified as an agonist or antagonist of P-gp activity and can be selected for further characterization.

Compound transport across a membrane in cultured cells can be monitored using known techniques, for instance the radio-labeling method outlined in Schinkel et al. *J. Clin. Invest.* 96:1698-1705, 1995. Briefly, cells are grown in complete medium including L-glutamine, penicillin, streptomycin, and FCS and seeded on microporous polycarbonate membrane filters (3.0 µM pore size, 24.5 mm diameter, Transwell™ 3414, Costar Corp., Cambridge, Md.) at a density of $2\times10^6$ cells per well. Medium at either the apical or basal side of the cell layer is replaced with complete medium containing the appropriate concentration of radiolabeled drug or drug candidate and cells are incubated at 37° C. in 5% $CO_2$. Subsequently, 50 µl aliquots are taken from each compartment at various time intervals, for instance 1, 2, 3, and 4 hours. The appearance of radioactivity in the non-treated compartment is measured and presented as the fraction of total radioactivity added at the beginning of the experiment.

In some methods employing the provided cell systems, the level of radioactive effector compound transported into the cells is compared between cells that received treatment with a test compound (e.g., a putative or potential P-gp activity agonist or antagonist) and those that did not receive such treatment, or between cells that received different test compound treatments (for instance, as to the test compound used, the method or timing of application, the amount applied, and so forth).

Methods of monitoring compound-uptake will in some instances be influenced by the compounds being studied.

This disclosure provides a mutation in the canine (particularly collie) mdr1 gene, which results in a truncation of P-gp and leads to extreme sensitivity to ivermectin in animals homozygous for this mutant allele. The disclosure further provides methods and kits for screening for this mutation, in order to identify animals susceptible to toxicity from ivermectin and other neurotoxic compounds that interact with the P-gp transport protein. Also provided are whole-animal and cell-based model systems for studying compound interactions with P-gp using the mdr1 truncation mutation described herein. It will be apparent that the precise details of the methods described may be varied or modified without departing from the spirit of the described invention. We claim all such modifications and variations that fall within the scope and spirit of the claims below.

The invention claimed is:

1. A method of making a treatment decision for a canine subject, comprising:

determining whether a gene-truncation mutation in a mdr1-encoding sequence or a truncated P-gp encoded by the gene-truncation mutation in the mdr1-encoding sequence is present in the canine subject; and making a treatment decision for the canine subject, wherein presence of the gene-truncation mutation or truncated P-gp influences the treatment decision of whether to provide the canine subject with a drug depending on whether the drug is excluded from a cell or an organ by P-gp, and wherein the gene-truncation mutation is at residue 294-297 of SEQ ID NO: 1 (the canine mdr1 cDNA) and results in a non-functional P-gp protein.

2. The method of claim 1, wherein the drug is a neurokinin receptor antagonist, anti-emetic agent, beta-adrenergic receptor antagonist, antiinfective agent, antiepileptic agent, antineoplastic agent, analgesic agent, anti-psychotic agent, or anti-depressive agent, and wherein functional P-gp excludes the drug from the cell or the organ.

3. The method of claim 2, wherein the drug is an anti-infective agent, and the anti-infective agent is an antiviral agent.

4. The method of claim 1, wherein the drug is ivermectin.

5. The method of claim 1, wherein determining whether the gene-truncation mutation is present in the canine subject comprises subjecting DNA or RNA from the canine subject to restriction digestion, probe hybridization, nucleic acid amplification, or nucleotide sequencing.

6. The method of claim 5, wherein determining whether the gene-truncation mutation is present in the canine subject is by subjecting DNA or RNA from the canine subject to nucleic acid amplification using a oligonucleotide primer.

7. The method of claim 5, wherein determining whether the gene-truncation mutation is present in the canine subject is by performing an oligonucleotide ligation assay.

8. The method of claim 1, wherein determining whether the gene-truncation mutation is present in the canine subject comprises:

obtaining from the canine subject a test sample of DNA comprising the mdr1 sequence; and contacting the test sample with at least one nucleic acid probe for the mdr1 gene truncation mutation at residue 294-297 of SEQ ID NO: 1.

9. The method of claim 1, wherein determining whether the truncated P-gp is present in a sample from the canine subject comprises reacting at least one P-gp molecule contained in the sample from the canine subject with a P-gp-specific binding agent to form a P-gp:agent complex.

10. The method of claim 9, wherein the binding agent is an antibody.

11. The method of claim 9, further comprises detecting the P-gp:agent complex by Western blot assay, ELISA, or other immunoassay technique.

12. The method of claim 1, wherein the treatment decision relates to a decision of whether to provide the drug to the canine subject.

13. The method of claim 12, wherein the drug is ivermectin.

\* \* \* \* \*

UNITED STATES PATENT AND TRADEMARK OFFICE
CERTIFICATE OF CORRECTION

PATENT NO. : 7,393,643 B2  
APPLICATION NO. : 10/896434  
DATED : July 1, 2008  
INVENTOR(S) : Mealey Page 1 of 2

It is certified that error appears in the above-identified patent and that said Letters Patent is hereby corrected as shown below:

On the Cover Page:

Item (56) Other Publications (1st column line 10):

"Pharmacol. Therp. vol." should read --Pharmacol. Therap. vol.--.

Item (56) Other Publications (2nd column line 33):

"drug refractory All," should read --drug refractory ALL,--.

Item (56) Other Publications (2nd column line 49):

"of the mrd1 gene" should read --of the mdr1 gene--.

Column 1, line 41, "endot-helial" should read --endo-thelial--.

Column 2, line 41, "1997, 1997" should read --1997--.

Column 2, line 67, "1989 Paul" should read --1989; Paul--.

Column 3, line 9, "Roher" should read --Rohrer--.

Column 3, line 28, "P-pg" should read --P-gp--.

Column 5, line 16, "beta-adr-energic" should read --beta adrenergic--.

Column 8, line 9, "Perlin-Elmer" should read --Perkin-Elmer--.

Column 8, Table 1, "294-2961" should read --2942-2961--.

Column 13, line 19, "80:3340, 1985" should read --80:33-40, 1985--.

Column 15, line 12, "ivernectin" should read --invermectin--.

Column 21, line 55, "on after" should read --after--.

UNITED STATES PATENT AND TRADEMARK OFFICE
CERTIFICATE OF CORRECTION

PATENT NO. : 7,393,643 B2
APPLICATION NO. : 10/896434
DATED : July 1, 2008
INVENTOR(S) : Mealey It is certified that error appears in the above-identified patent and that said Letters Patent is hereby corrected as shown below:

Column 22, line 60, "0.11 mM" should read --0.1 mM--.

Column 23, line 18, "Ann Arbor, Minn." should read --Ann Arbor, MI--.

Column 25, lines 2-3, "AAACATGACGTTTG-CAAAT" should read

--AAACATGACGCTTTGCAAAT--.

Column 28, line 62, "Cambridge, Md." should read --Cambridge, MA--.

Signed and Sealed this

Thirty-first Day of March, 2009

JOHN DOLL
*Acting Director of the United States Patent and Trademark Office*